US010495550B2

(12) United States Patent
Sun

(10) Patent No.: US 10,495,550 B2
(45) Date of Patent: Dec. 3, 2019

(54) IDENTIFICATION OF CHEMICALS IN A SAMPLE USING GC/SAW AND RAMAN SPECTROSCOPY

(71) Applicant: Pulmostics Limited, Dublin (IE)

(72) Inventor: Yin Sun, Bridgewater, NJ (US)

(73) Assignee: Pulmostics Limited, Dublin (IE)

(*) Notice: Subject to any disclaimer, the term of this patent is extended or adjusted under 35 U.S.C. 154(b) by 0 days.

(21) Appl. No.: 15/545,215

(22) PCT Filed: May 18, 2017

(86) PCT No.: PCT/US2017/033270
§ 371 (c)(1),
(2) Date: Jul. 20, 2017

(87) PCT Pub. No.: WO2017/201250
PCT Pub. Date: Nov. 23, 2017

(65) Prior Publication Data
US 2018/0224354 A1 Aug. 9, 2018

Related U.S. Application Data

(60) Provisional application No. 62/339,344, filed on May 20, 2016.

(51) Int. Cl.
*G01N 1/10* (2006.01)
*G01N 1/22* (2006.01)
*G01N 21/65* (2006.01)
*G01N 29/02* (2006.01)
*G01N 30/74* (2006.01)
*G01N 30/76* (2006.01)
*G01N 30/78* (2006.01)
(Continued)

(52) U.S. Cl.
CPC ............. *G01N 1/10* (2013.01); *G01N 1/2202* (2013.01); *G01N 21/65* (2013.01); *G01N 29/022* (2013.01);
(Continued)

(58) Field of Classification Search
CPC ........ G01N 1/10; G01N 1/2202; G01N 21/65; G01N 2291/02809; G01N 29/022;
(Continued)

(56) References Cited

U.S. PATENT DOCUMENTS 5,455,673 A * 10/1995 Alsmeyer ................. G01J 3/44
356/301
6,134,944 A   10/2000 Yu et al.
(Continued)

OTHER PUBLICATIONS

Ocean Optics: Raman Spectroscopy Equipment Ocean Optics Spectrometers.html 2089-2019 (Year: 2019)*
(Continued)

*Primary Examiner* — Francis C Gray
(74) *Attorney, Agent, or Firm* — Stetina Brunda Garred & Brucker

(57) ABSTRACT

A method for identification of chemicals in a sample using a gas chromatograph, a surface acoustic wave (SAW) sensor coupled with the gas chromatograph to define a gas chromatography (GC)/SAW system, and a Raman spectrometer. The method includes receiving SAW frequency response data generated by the SAW sensor, receiving Raman spectrum data generated by the Raman spectrometer, producing a Raman spectrum corresponding to an eluted component of interest based upon an integration of the Raman spectrum data, identifying a set of one or more candidate chemicals for the eluted component of interest based on a corresponding peak of the SAW frequency response data, and searching a Raman database for a match between the produced Raman spectrum and a chemical in the Raman database from among the set of candidate chemicals for the eluted component of interest.

20 Claims, 14 Drawing Sheets

(51) Int. Cl.
G01N 29/036 (2006.01)
G01N 30/86 (2006.01)

(52) U.S. Cl.
CPC ............ G01N 29/036 (2013.01); G01N 30/74 (2013.01); G01N 30/76 (2013.01); G01N 30/78 (2013.01); G01N 30/8675 (2013.01); G01N 2291/02809 (2013.01)

(58) Field of Classification Search
CPC ...... G01N 29/036; G01N 30/74; G01N 30/76; G01N 30/78; G01N 30/8675
See application file for complete search history.

(56) References Cited

U.S. PATENT DOCUMENTS

| | | | | |
|---|---|---|---|---|
| 2004/0127778 | A1* | 7/2004 | Lambert | A61B 5/14532 600/318 |
| 2005/0171436 | A1* | 8/2005 | Clarke | A61B 5/0075 600/476 |
| 2007/0272852 | A1* | 11/2007 | Miller | G01N 27/624 250/288 |
| 2009/0189064 | A1* | 7/2009 | Miller | G01N 27/624 250/282 |
| 2010/0291711 | A1* | 11/2010 | Atashbar | G01N 27/127 436/524 |
| 2012/0198912 | A1 | 8/2012 | Ewing et al. | |
| 2013/0157254 | A1* | 6/2013 | Sengupta | G01N 21/658 435/5 |

OTHER PUBLICATIONS

Ludmila Meciarova, Silvia Vilcekova and Magdalena Balintova, "Measurement of VOCs with a Portable GC/Saw Detector", The Italian Association of Chemical Engineering, 2014, pg. 283-288, vol. 40.

* cited by examiner

| Time | SAW Frequency Response Data | Raman Spectrum Data |
|---|---|---|
| $t_1$ | $S_1$ | $R_1$ |
| $t_2$ | $S_2$ | $R_2$ |
| ⋮ | ⋮ | ⋮ |
| $t_n$ | $S_n$ | $R_n$ |

FIG. 5

IDENTIFICATION OF CHEMICALS IN A SAMPLE USING GC/SAW AND RAMAN SPECTROSCOPY

CROSS-REFERENCE TO RELATED APPLICATION(S)

This application relates to and claims the benefit of U.S. Provisional Application No. 62/339,344 filed May 20, 2016 and entitled "APPARATUS FOR SAMPLE ANALYSIS WITH MULTIPLE SENSOR FUSION," the entire disclosure of which is hereby wholly incorporated by reference.

STATEMENT RE: FEDERALLY SPONSORED RESEARCH/DEVELOPMENT

Not Applicable

BACKGROUND

Technical Field

The present disclosure relates generally to identification of chemicals in a sample, and more particularly, to identification of chemicals through the use of gas chromatography (GC), a surface acoustic wave (SAW) sensor, and a Raman spectrometer system.

Related Art

Various devices for qualitative identification and/or quantitative measurement of chemicals in a sample make use of gas chromatography for separation of the sample into components. A vaporized sample passes through a GC column of a gas chromatograph in which different components of the sample are retained for different lengths of time depending on their chemical-physical properties. As each component elutes from the GC column, its retention time is measured by a detector. Chemical identification of each component is based on analysis of the measured retention time and the identified properties by the sensory technology. One of the most commonly used techniques, considered the standard in analytical chemistry, is GC/mass spectrometry (MS), in which a mass spectrometer is employed as the detector, making use of its additional capability of detecting ionized fragments of each separated component. However, there are some significant drawbacks of this technology, such as large size, high cost, and the fact that GC/MS systems are typically not portable.

Other examples of detectors that have been used with gas chromatography include photoionization detectors (PID), electron capture detectors (ECD), and SAW sensors (so-called GC/SAW systems). For these types of detectors, chemical identification is based solely on GC retention time, which has known limitations, such as the possibility of false identification in cases where components are not well separated by the gas chromatograph.

Another area of technology, conventionally unconnected to gas chromatography, is spectroscopy, in which a device measures changes in an electromagnetic spectrum before and after excitation of a sample with light. One such device is a Raman spectrometer, which measures Raman scattering, i.e. inelastic scattering of photons as molecules in the sample are excited to virtual energy states. Since such spectra are directly related to the molecular structure of the sample, chemical identification can be achieved with high accuracy. However, a high concentration of the chemical is typically needed.

BRIEF SUMMARY

The present disclosure contemplates various systems, methods, and apparatuses for overcoming the above drawbacks accompanying the related art. One aspect of the embodiments of the invention is a method for identification of chemicals in a sample. The method includes receiving surface acoustic wave (SAW) frequency response data generated by a SAW sensor of a gas chromatography (GC)/SAW system, the SAW frequency response data including one or more peaks corresponding respectively to one or more eluted components separated from a sample by a gas chromatograph of the GC/SAW system, receiving Raman spectrum data generated by a Raman spectrometer for the one or more eluted components, producing a Raman spectrum corresponding to an eluted component of interest from among the one or more eluted components based upon an integration of the Raman spectrum data, identifying a set of one or more candidate chemicals for the eluted component of interest based on the corresponding peak of the SAW frequency response data, and searching a Raman database for a match between the produced Raman spectrum and a chemical in the Raman database from among the set of candidate chemicals for the eluted component of interest.

Another aspect of the embodiments of the invention is a system for identification of chemicals in a sample. The system includes a gas chromatograph, a surface acoustic wave (SAW) sensor coupled with the gas chromatograph to define a gas chromatography (GC)/SAW system in which one or more eluted components separated from a sample by the gas chromatograph accumulate at a condensation spot on the SAW sensor, and a Raman spectrometer aligned with the condensation spot, Raman scattered light from one or more eluted components accumulated at the condensation spot being collectable by the Raman spectrometer. The system may further include an input interface communicatively coupled to the SAW sensor and the Raman spectrometer, the input interface being receptive to SAW frequency response data generated by the SAW sensor and including one or more peaks corresponding respectively to the one or more eluted components separated from the sample by the gas chromatograph, the input interface further being receptive to Raman spectrum data generated by the Raman spectrometer for the one or more eluted components, a spectrum producer communicatively coupled to the input interface, a Raman spectrum corresponding to an eluted component of interest from among the one or more eluted components being produced by the spectrum producer based upon an integration of the Raman spectrum data, a candidate chemical identifier communicatively coupled to the input interface, a set of one or more candidate chemicals for the eluted component of interest being identified by the candidate chemical identifier based on the corresponding peak of the surface acoustic wave frequency response data, and a Raman search engine communicatively coupled to the candidate chemical identifier and the spectrum producer, a Raman database being searched by the Raman search engine for a match between the produced Raman spectrum and a chemical in the Raman database from among the set of candidate chemicals for the eluted component of interest.

Another aspect of the embodiments of the invention is a non-transitory program storage medium on which are stored instructions executable by a processor or programmable circuit to perform operations for identification of chemicals in a sample. The operations include receiving surface acoustic wave (SAW) frequency response data generated by a SAW sensor of a gas chromatography (GC)/SAW system, the SAW frequency response data including one or more peaks corresponding respectively to one or more eluted components separated from a sample by a gas chromatograph of the GC/SAW system, receiving Raman spectrum data generated by a Raman spectrometer for the one or more eluted components, producing a Raman spectrum corresponding to an eluted component of interest from among the one or more eluted components based upon an integration of the Raman spectrum data, identifying a set of one or more candidate chemicals for the eluted component of interest based on the corresponding peak of the SAW frequency response data, and searching a Raman database for a match between the produced Raman spectrum and a chemical in the Raman database from among the set of candidate chemicals for the eluted component of interest.

The present disclosure will be best understood accompanying by reference to the following detailed description when read in conjunction with the drawings.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 5 is an example of SAW frequency response data and Raman spectrum data;

DETAILED DESCRIPTION

The present disclosure encompasses various embodiments of systems, methods, and apparatuses for identification of chemicals in a sample. The detailed description set forth below in connection with the appended drawings is intended as a description of the several presently contemplated embodiments of these methods, and is not intended to represent the only form in which the disclosed invention may be developed or utilized. The description sets forth the functions and features in connection with the illustrated embodiments. It is to be understood, however, that the same or equivalent functions may be accomplished by different embodiments that are also intended to be encompassed within the scope of the present disclosure. It is further understood that the use of relational terms such as first and second and the like are used solely to distinguish one from another entity without necessarily requiring or implying any actual such relationship or order between such entities.

Figure 1:
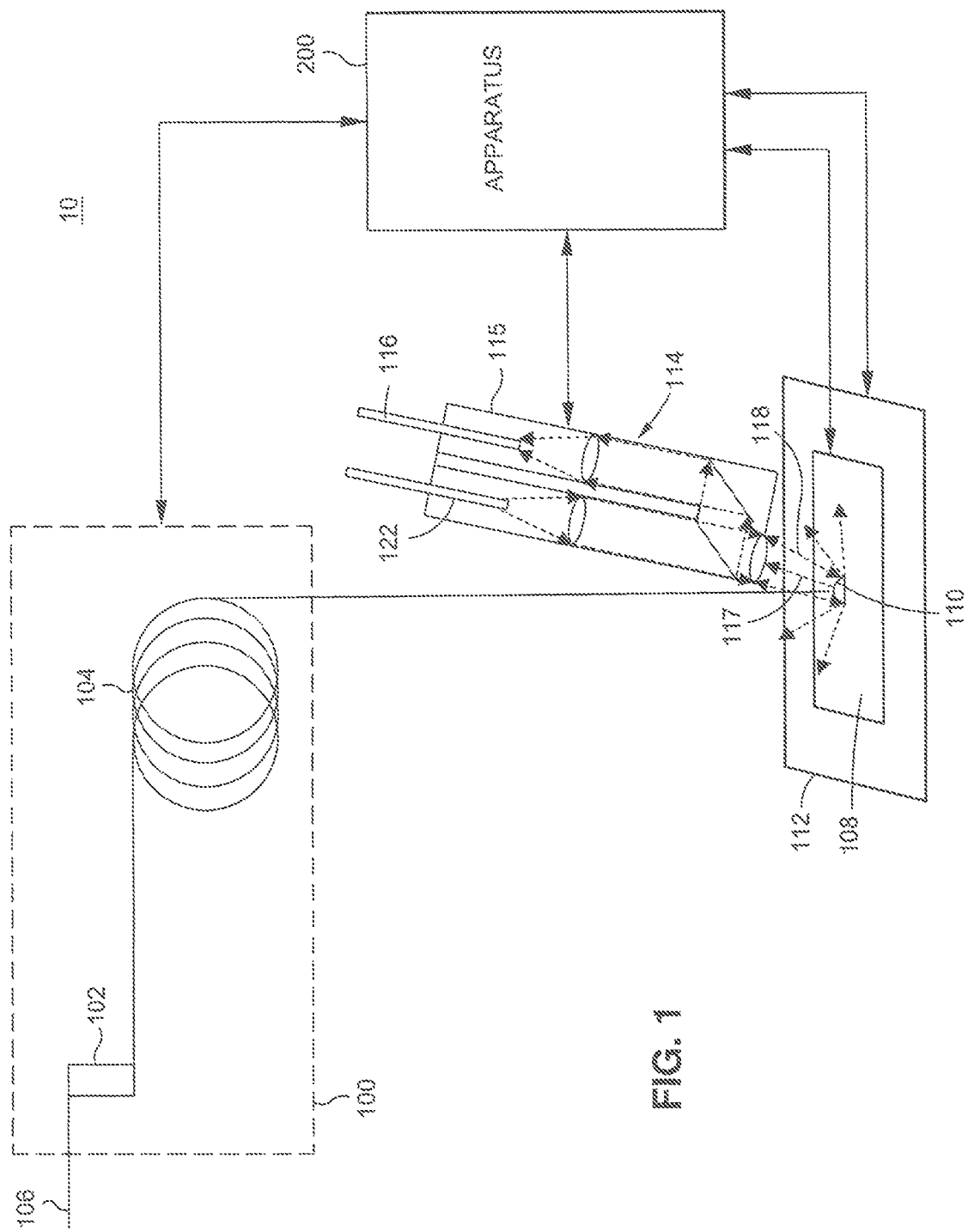
FIG. 1 illustrates a system for identification of chemicals in a sample according to an embodiment of the invention.

FIG. 1 illustrates a system 10 for identification of chemicals in a sample according to an embodiment of the present disclosure. The system 10 includes a gas chromatograph 100, which may include an injection port 102 and a gas chromatography (GC) column 104. Upon being injected into the gas chromatograph 100 via the injection port 102, a vaporized sample is carried by a carrier gas 106 through the GC column 104, where different components of the sample are retained for different lengths of time depending on their chemical-physical properties. The system 10 illustrated in FIG. 1 further includes a surface acoustic wave (SAW) sensor 108 coupled with the gas chromatograph 100 to define a GC/SAW system in which one or more eluted components separated from the sample by the gas chromatograph 100 accumulate at a condensation spot 110 on the SAW sensor 108. The SAW sensor 108 may, for example, be arranged close to the output of the GC column 104 such that the condensation spot 110 is close to the size of an internal dimension of the GC column 104. Chemical components of the sample eluting from the GC column 104 arrive at the condensation spot 110, where they condense as long as the temperature of the SAW sensor 108 is lower than the dew point of the chemical component. To this end, the system may include a thermoelectric cooler 112 by which the temperature of the SAW sensor 108 can be adjusted. Electronics (not shown) associated with the SAW sensor 108 may generate SAW frequency response data including one or more peaks corresponding respectively to one or more chemical components that condense at the condensation spot 110 as they elute from the GC column 104.

The system 10 of FIG. 1 further includes a Raman spectrometer 114 aligned with the condensation spot 110 so as to collect Raman scattered light 117 from one or more eluted components accumulated at the condensation spot 110. The head or probe 115 of the Raman spectrometer 114, which houses the optical elements (e.g. lenses, filters, mirrors) of the Raman spectrometer 114, may be positioned above the SAW sensor 108 at a distance of a few millimeters to a few centimeters and at an angle so as not to interfere with the accumulation of the chemical components at the condensation spot 110. The head or probe 115 may be of coaxial design, with one or more optical elements focusing an excitation laser 118 introduced through an excitation optical fiber 122 at the condensation spot 110 and thereafter receiving Raman scattered light 117 from the condensation spot 110 to be collected by a collection optical fiber 116. The positions of the GC column 104 and SAW sensor 108 may be predetermined and fixed, allowing for high precision focusing of the excitation laser 118 at the condensation spot 110. Raman scattered light 117 collected by the collection optical fiber 116 may be subsequently incident on a Raman sensor (not shown), e.g. a charged coupled device (CCD) and used to generate Raman spectrum data of one or more chemical components that condense at the condensation spot 110 as they elute from the CD column 104. Raman spectrum data may be generated at a sampling frequency matching that of the SAW frequency response data to produce corresponding data sets.

The gas chromatograph 100, SAW sensor 108, and Raman spectrometer 114 may be of any type known in the art. Selection of the injection port 102, GC column 104, and carrier gas 106 may be in accordance with known principles of gas chromatography and GC/SAW systems and may depend on the nature of the sample and the particular application. For example, the diameter of the GC column and other aspects of the GC/SAW system may be selected to support fast GC.

Lastly, the system of FIG. 1 includes an apparatus 200 which may support the qualitative and/or quantitative identification of chemicals in the sample. The apparatus 200 may be operatively connected to each of the other components of the system 10, including the SAW sensor 108 and the Raman spectrometer 114, as well as other system components such as the gas chromatograph 100 and/or the thermoelectric cooler 112. Thus, the apparatus 200 may be used for post-processing of SAW frequency response data and Raman spectrum data and/or control of the various system components in accordance with results of processing by the apparatus 200 and/or user input to the apparatus 200, in which case the apparatus 200 may serve as a user terminal. The operative connection of the apparatus 200 may be a physical (e.g. wired) connection, a wireless connection over a network, or a purely conceptual connection such as in a case where data generated by the SAW sensor 108, Raman spectrometer 114, etc. is then accessed, processed, etc. by the apparatus 200 (e.g. after being transferred by some data storage medium) in the case of post-processing, or vice versa in the case of system control by the apparatus 200.

Figure 2:
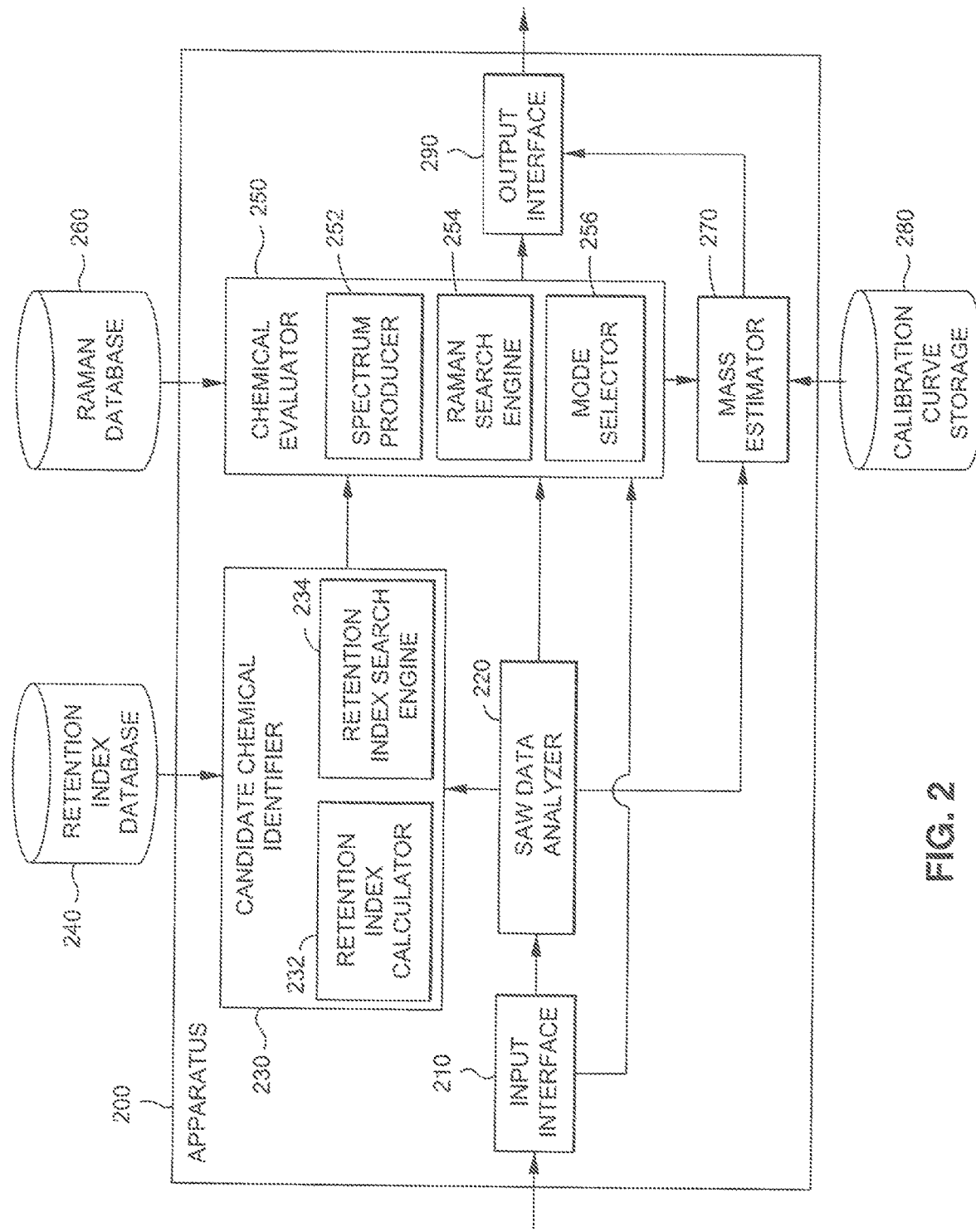
FIG. 2 illustrates an example apparatus 200 for identification of chemicals in a sample according to an embodiment of the invention.

FIG. 2 illustrates an example apparatus 200 for identification of chemicals in a sample according to an embodiment of the invention. The apparatus 200 receives SAW frequency response data and Raman spectrum data, integrates the Raman spectrum data to produce a Raman spectrum corresponding to an eluted component of interest, identifies a set of candidate chemicals using the SAW frequency response data, and searches a Raman database for a match between the Raman spectrum and one of the candidate chemicals. On the basis of such search, the apparatus 200 may identify the chemical of the eluted component of interest (e.g. in the case of a successful search) and/or adjust settings of the other system components of FIG. 1. The apparatus 200 includes an input interface 210, a SAW data analyzer 220, a candidate chemical identifier 230, a chemical evaluator 250, a mass estimator 270, and an output interface 290 and may further include or have access to a retention index database 240, a Raman database 260, and a calibration curve storage 280.

The input interface 210 receives SAW frequency response data generated by the SAW sensor 108 of the GC/SAW system, the SAW frequency response data including one or more peaks corresponding respectively to one or more eluted components separated from a sample by the gas chromatograph 100 of the GC/SAW system. The input interface 210 further receives Raman spectrum data generated by the Raman spectrometer 114 for the one or more eluted components. The SAW frequency response data is a representation of the frequency response of the SAW sensor 108 as a function of time and may be in the form of, for example, frequency in Hz versus GC retention time in seconds. Thus, in a case where the sampling frequency of the SAW sensor 108 is 50 Hz, the SAW frequency response data may include a series of frequency response samples at 20 millisecond intervals. The frequency response of the SAW sensor 108 may be, for example, a change in an oscillation frequency due to the accumulation of an eluted chemical component on the SAW sensor 108. The Raman spectrum data is a representation of Raman scattered light 117 received by the Raman spectrometer 114 and incident on a Raman sensor thereof and may be in the form of, for example, intensity in counts per second as a function of Raman shift in cm-1 versus GC retention time in seconds. Thus, in a case where the sampling frequency of the Raman spectrometer 114 is 50 Hz, the Raman spectrum data may include a series of Raman spectrum samples at 20 millisecond intervals.

The input interface 210 may receive the SAW frequency response data and Raman spectrum data from outside the apparatus 200. For example, the input interface 210 may receive the SAW frequency response data and Raman spectrum data directly from the other system components of FIG. 1, e.g. by wired or wireless connection with the SAW sensor 108 and the Raman spectrometer 114 or associated electronics (not shown) thereof. Alternatively, the SAW frequency response data and Raman spectrum data can be received from an external storage or received from a computer or server through a network such as the Internet, WAN, and/or LAN.

The SAW data analyzer 220 identifies the one or more peaks of the SAW frequency response data and identifies one or more valleys of the SAW frequency response data. For example, the SAW data analyzer 220 may identify peaks and valleys by approximating the SAW frequency response data with a polynomial, taking the derivative of the polynomial, and finding the points where the derivative of the polynomial is equal to zero (corresponding to maxima and minima of the polynomial). The SAW data analyzer 220 may thus characterize each of the one or more peaks and each of the one or more valleys by its GC retention time or sample number. The SAW data analyzer 220 may further characterize each of the one or more peaks by a peak height and/or a peak area (e.g. by integrating the polynomial approximating the SAW frequency response data from valley to valley around the peak).

The SAW data analyzer 220 may also evaluate whether adjacent peaks of the one or more peaks are partially overlapping. Partially overlapped peaks, as distinguished from fully overlapped peaks or non-overlapped peaks, may be those peaks that are so close together that accurate Raman spectra of the chemical components may be difficult to produce, while being far enough apart that the peaks are separately discernible by the SAW data analyzer 220. More specifically, if two peaks are so close together that the SAW data analyzer 220 does not identify a valley between them, the peaks are considered fully overlapped peaks and are indistinguishable (at this stage) from non-overlapped peaks. The SAW data analyzer 220 does not characterize such fully overlapped peaks as partially overlapped peaks. If two peaks are far enough apart that the SAW data analyzer 220 identifies a valley between them, the SAW data analyzer 220 may characterize the peaks as partially-overlapped peaks or not based on predetermined criteria. For example, the SAW data analyzer 220 may evaluate whether such adjacent peaks are partially overlapping by evaluating, with respect to the adjacent peaks, whether the height of the valley between the adjacent peaks exceeds a valley height threshold. If the valley separating the adjacent peaks is too high, it can be understood that the valley does not represent the first chemical component evaporating completely from the condensation spot 110 before the second chemical component begins to condense but rather that there is some overlap during which both chemical components are present at the condensation spot 110 (the first chemical beginning to evaporate while the second chemical begins to condense). As another example, the SAW data analyzer 220 may evaluate whether adjacent peaks are partially overlapping by evaluating, with respect to the adjacent peaks, whether the adjacent peaks are closer together than a peak distance threshold. In this way, a simple time relationship between the adjacent peaks (e.g. how many milliseconds apart) can roughly indicate whether some overlap of the chemical components is likely.

The candidate chemical identifier 230 identifies a set of one or more candidate chemicals for an eluted component of interest based on the corresponding peak of the SAW frequency response data. The candidate chemical identifier 230 may, for example, identify sets candidate chemicals for all of the eluted components, i.e. a set of candidate chemicals for each of the peaks found by the SAW data analyzer 220. Or, in a case where some peaks are uninteresting, the candidate chemical identifier 230 may identify sets of candidate chemicals for only a subset of the peaks found by the SAW data analyzer 220. The candidate chemical identifier 230 includes a retention index calculator 232 and a retention index search engine 234.

The retention index calculator 232 calculates a retention index for the eluted component of interest from the corresponding peak of the SAW frequency response data. A GC retention time of a peak found by the SAW data analyzer 220 may be converted into a retention index, e.g. Kovats retention index, that is independent of the specific gas chromatograph 100 and its operating conditions. The retention index calculator 232 may calculate the retention index by known methods. For example, n-alkanes may be injected into the gas chromatograph 100 together with the sample, and the peaks of the eluted n-alkanes may be found by the SAW data analyzer 220 together with the peaks corresponding to the chemical components of the sample. The retention index calculator 232 may calculate the retention index of a given peak of the sample based on its relationship to the peaks of the eluted n-alkanes.

The retention index database 240 may include, for example, a table of chemicals and corresponding known retention indices. The retention index search engine 234 searches the retention index database 240 for one or more matches between the determined retention index and chemicals in the retention index database 240. In this way, the candidate chemical identifier 230 may identify a set of one or more candidate chemicals for each of the eluted components.

In the example of the candidate chemical identifier 230 shown in FIG. 2, identification of candidate chemicals may be achieved with the use of retention indices. To this end, the candidate chemical identifier 230 includes the retention index calculator 232 and the retention index search engine 234 and has access to the retention index database 240. However, other methods of identifying candidate chemicals is known in the art, such as direct comparison of retention times with retention times of known chemicals eluted from the same gas chromatograph 100 under similar conditions. Therefore, in some embodiments, the candidate chemical identifier 230 may omit the retention index calculator 232 and the retention index search engine 234, and may thus have no need to access the retention index database 240.

The chemical evaluator 250 receives the analyzed SAW frequency response data from the SAW data analyzer 220 and the set of one or more candidate chemicals for an eluted component of interest (or for all or any subset of the eluted components) from the candidate chemical identifier 230. The chemical evaluator 250 further receives the Raman spectrum data from the input interface 210. On the basis of these inputs, the chemical evaluator 250 determines the identity of an eluted component of interest by matching a Raman spectrum of the component to a known spectrum of one of the candidate chemicals for the component. The chemical evaluator 250 includes a spectrum producer 252, a Raman search engine 254, and a mode selector 256.

The spectrum producer 252 integrates the Raman spectrum data to produce a Raman spectrum corresponding to an eluted component of interest from among the one or more eluted components. For example, using the peaks and valleys found by the SAW data analyzer 220, the spectrum producer 252 may integrate the Raman spectrum data from a valley immediately preceding the peak corresponding to the eluted component of interest to a valley immediately following the peak corresponding to the eluted component of interest. For instance, if the peak of interest occurs in the SAW frequency response data at t=5500 milliseconds, and the surrounding valleys are at t=5000 milliseconds and t=6000 milliseconds, the spectrum producer 252 may integrate the samples of the Raman spectrum data from a sample corresponding to t=5000 milliseconds to a sample corresponding to t=6000 milliseconds. As a specific example, in a case where both the SAW frequency response data and the Raman spectrum data are generated at the same sampling frequency of 50 Hz, the spectrum producer 252 may integrate the Raman spectrum data from all of the samples t=5000, t=5020, t=5040, t=5980, and t=6000 to produce a Raman spectrum corresponding to the component represented by the peak at t=5500.

The Raman database 260 may include, for example, a table of chemicals and corresponding known Raman spectra. The Raman search engine 254 searches the Raman database 260 for a match between the Raman spectrum produced by the spectrum producer 252 and a chemical in the Raman database 260 from among the set of candidate chemicals for the eluted component of interest. In this way, the chemical evaluator 250 may identify the chemical of the eluted component of interest with greater precision than is possible by the candidate chemical identifier 230 alone. Meanwhile, because the candidate chemical identifier 230 narrows the field of possibilities down to one or more candidate chemicals, the chemical evaluator 250 does not need to search the entire contents of the Raman database 260, and does not need to produce a Raman spectrum that distinguishes the chemical component of interest from every known Raman spectrum in the Raman database 260. Thus, time may be saved, and it may also be possible to relax settings and design parameters of the Raman spectrometer 114.

The above-described functionality of the spectrum producer 252 and Raman search engine 254 may represent a straightforward simple case, in which a Raman spectrum is produced by valley-to-valley integration and a match is easily found in the Raman database 260. This is typical when peaks of the SAW frequency response data are non-overlapped. In addition, the above-described functionality may also represent a part of a procedure for determining a chemical of an eluted component in a more complicated case, such as where peaks of the SAW frequency response data are partially-overlapped or fully-overlapped.

In view of the possibility of partially-overlapped or fully-overlapped peaks, the mode selector 256 selects between a plurality of chemical decision modes including a non-overlap decision mode, a partial-overlap decision mode, and a full-overlap decision mode, or between any two of these three modes. For example, in a case where the SAW data analyzer 220 evaluates whether adjacent peaks of the SAW frequency response data are partially overlapping, the mode selector 256 may select, with respect to the adjacent peaks, between a non-overlap decision mode and a partial-overlap decision mode based on a result of the evaluation by the SAW data analyzer 220. Thus, the mode selector 256 may select a partial-overlap decision mode for adjacent peaks that are evaluated as being partially overlapping. The mode selector 256 may select (e.g. by default) a non-overlap decision mode for other peaks. As described in more detail below, the partial-overlap decision mode affects the procedure by which the chemical evaluator 250 determines the identity of an eluted component of interest.

As another example, after the Raman search engine 254 searches the Raman database for a match between a Raman spectrum produced by the spectrum producer 252 and a chemical in the Raman database 260, the chemical evaluator 250 may evaluate whether a match was found. A failure to find a match may indicate that the peak in the SAW frequency response data corresponding to the eluted component of interest is actually the result of more than one eluted component with substantially the same GC retention time. That is, what appears to be a single peak may actually be a superimposition of two or more fully overlapped peaks. Thus, by evaluating whether a match is found, the chemical evaluator 250 may evaluate whether the peak corresponding to the eluted component of interest is a combination of two or more fully overlapped peaks. The mode selector 256 may select, with respect to the peak corresponding to the eluted component of interest, between a non-overlap decision mode and a full-overlap decision mode based on a result of the evaluation by the chemical evaluator 250. Thus, the mode selector 256 may select a full-overlap decision mode for a peak that is evaluated as being a combination of two fully overlapping peaks. The mode selector 256 may select (e.g. by default) a non-overlap decision mode for other peaks. As described in more detail below, the full-overlap decision mode affects the procedure by which the chemical evaluator 250 determines the identity of an eluted component of interest.

A failure to find a match may indicate scenarios other than fully overlapped peaks. For example, it may indicate that the Raman database 260 is incomplete or that one or more of the system components (e.g. the gas chromatograph 100, the SAW sensor 108, the Raman spectrometer 114, the thermoelectric cooler 112, etc.) is not functioning correctly or has insufficient capability or settings (e.g. sampling frequency, resolution, signal-to-noise, etc.) to identify the chemical component. Thus, an evaluation by the chemical evaluator 250 that a match has not been found may also be a basis for adjusting various settings of the system 10 shown in FIG. 1. For example, the apparatus 200 may automatically adjust system settings or may produce an error report to be acted on by some external system or user.

The mass estimator 270 estimates a mass of an eluted component of interest based on the corresponding peak of the SAW frequency response data. As explained above, the SAW data analyzer 220 may characterize each of the one or more peaks of the SAW frequency response data by a peak height and/or a peak area. Meanwhile, the calibration curve storage 208 may store calibration curves for various chemicals, each calibration curve mapping peak height or peak area to mass or other quantitative measure (e.g. concentration) in a known relationship for that chemical. Upon the successful identification of the eluted component of interest by the chemical evaluator 250, the mass estimator 270 may compare the peak (e.g. height or area) corresponding to the eluted component of interest to a calibration curve stored in the calibration curve storage 280, thereby producing an estimate of the mass or other quantitative measure of the eluted component of interest.

The output interface 290 outputs one or more of the various outputs of the apparatus 200 for use by a downstream device or user. For example, the outputs may be stored, uploaded to a server, printed, or otherwise made available for viewing or analysis. The various outputs of the apparatus 200 include, for example, singly or in combination, an identification of one or more chemical components (e.g. an eluted component of interest) of the sample as determined by the chemical evaluator 250, a mass or other quantitative measure of one or more identified chemical components of the sample as estimated by the mass estimator 270, the analyzed SAW frequency response data from the SAW data analyzer 220, error reports related to failed match attempts, etc. Such outputs may also be displayed on a screen in relation to a user query as an intermediate step in a process performed by the apparatus 200.

Outputs from the output interface 290 may further include control commands issued by the apparatus 200 directly to other system components of the system shown in FIG. 1. For example, the apparatus 200 may, via the output interface 290, adjust a temperature of the SAW sensor 108 with the thermoelectric cooler 112 based on a result of the evaluation by the chemical evaluator 250 as to whether a match was found in the Raman database 260. In this way, after the chemical evaluator 250 has exhausted its efforts to determine the chemical of an eluted component of interest (e.g. both the non-overlap and full-overlap decision modes have failed to find a match for a peak that is not partially overlapped), the apparatus 200 may lower the temperature of the SAW sensor 108 to effect a more effective condensation of the chemical (allowing for more samples of Raman spectrum data) in a subsequent run of the system. As another example, the apparatus 200 may raise the temperature of the SAW sensor 108 to effect shorter condensation times in a case where there is an undesirable number of partially-overlapped peaks in the SAW frequency response data (e.g. a number of partially-overlapped peaks, as determined by the SAW data analyzer 220, that exceeds a threshold).

Figure 3:
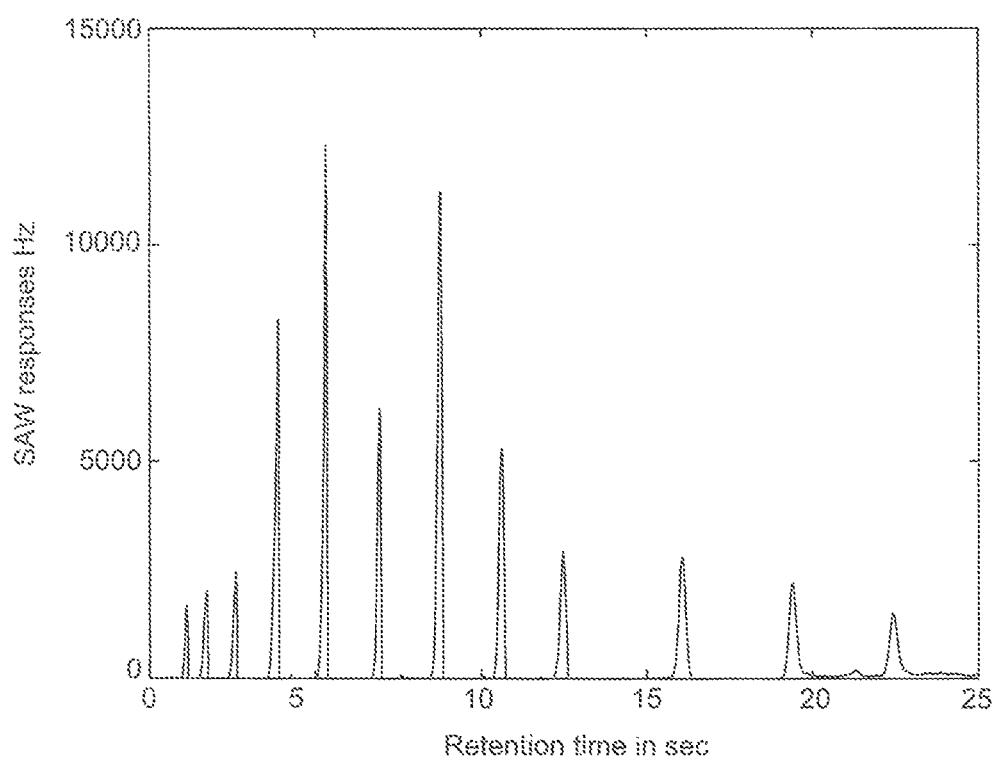
FIG. 3 is a graphical representation of an example of SAW frequency response data.

FIG. 3 is a graphical representation of an exemplary set of SAW frequency response data. As each chemical component of the sample elutes from the GC column 104, the SAW sensor 108 (or associated electronics, not shown) exhibits a SAW frequency response (shown in Hz on the y-axis) due to the accumulation of the eluted chemical component on the SAW sensor 108. The shape of each peak (e.g. height and area) is determined in part by the quantity (e.g. mass) of the component in the sample, as well as the temperature of the SAW sensor 108 in relation to the dew point of the component, which affects the width of the peak as the component accumulates on the SAW sensor 108 for a longer or shorter period of time.

The highest peak in FIG. 3 is centered at around 5500 milliseconds on the x-axis, indicating a retention time of approximately 5500 milliseconds, which may be measured from some initial time such as the moment the sample is injected into the gas chromatograph 100. Other peaks may correspond to other chemical components in the sample and known chemicals injected with the sample for purposes of determining retention indices (e.g. n-alkanes). SAW frequency response data like the example shown in FIG. 3 may be generated by the SAW sensor 108 or associated electronics in various forms (not necessarily as a graphical representation as shown) and thereafter or concurrently received by the input interface 210 of the apparatus 200 for processing by the apparatus 200.

Figure 4:
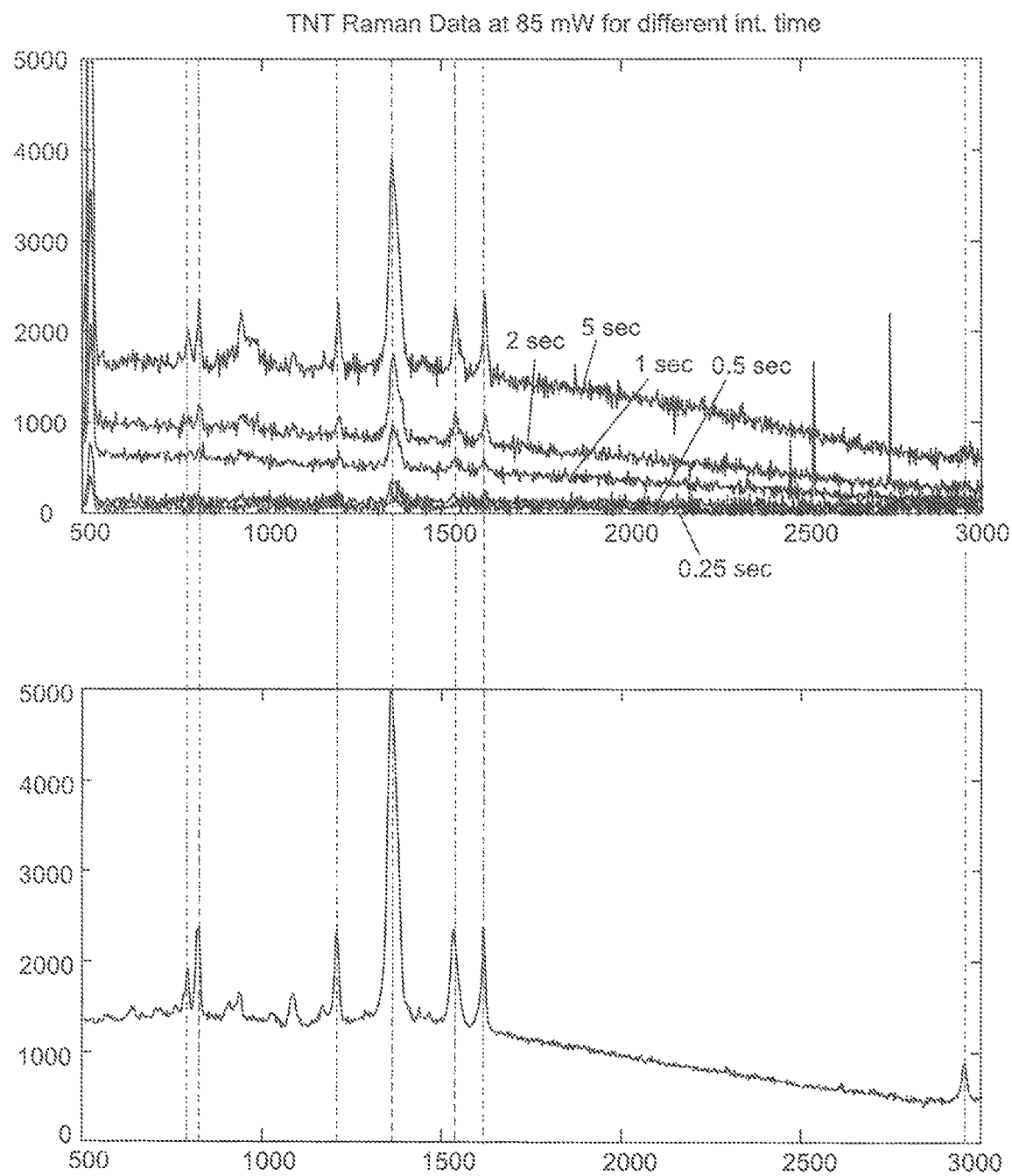
FIG. 4 is a graphical representation of an example of integrated Raman spectrum data with different integration times (upper plots), together with a known Raman spectrum (lower plot)

FIG. 4 is a graphical representation of an example of integrated Raman spectrum data with different integration times (upper plots), together with a known Raman spectrum (lower plot). The example in FIG. 4 is for a 3 nanogram sample of trinitrotoluene (TNT). The y-axis is Raman scattering intensity in counts per second, and the x-axis is Raman shift in cm-1. The integrated Raman spectrum data is shown for five integration times, 0.25 seconds, 0.5 seconds, 1 second, 2 seconds, and 5 seconds. As illustrated by the vertical lines connecting the upper plots to the lower plot, matching of integrated Raman spectrum data to a known Raman spectrum can be achieved by matching spikes in the spectra. In the apparatus 200, the matching as shown in FIG. 4 may be performed by the Raman search engine 254 as part of searching for a match for a peak corresponding to an eluted component of interest.

As can be seen, matching may be achievable in this case with as little as 2 seconds integration time, with the signal-to-noise ratio deteriorating at 1 second and below. Typically, peak width is longer than 2 seconds for a gas chromatography system, as determined by the length of the GC column 104, the temperature of the gas chromatograph 100, and the flow rate of the carrier gas 106. In the system shown in FIG. 1, the peak width of the SAW frequency response data generated by the GC/SAW system determines the maximum integration time of the Raman spectrum data for a given peak. This is because the Raman spectrum data for a given eluted component is gathered while the eluted component remains condensed on the SAW sensor 108 and until it evaporates. Thus, a longer than 2 seconds peak width typically means that Raman matching should be possible, but this may ignore the possibility of partially or fully overlapped peaks. In addition to addressing partially and fully overlapped peaks using partial-overlap and full-overlap decision modes to be described in more detail below, the disclosed system contemplates further controlling peak width by adjusting the temperature of the SAW sensor 108 with the thermoelectric cooler 112, which may be done automatically by or with reference to the output of the apparatus 200 as explained above. By adjusting the temperature of the SAW sensor 108 and through the use of the partial-overlap and full-overlap decision modes described with respect to the chemical evaluator 250, adequate integration time for matching is achievable.

Integrated Raman spectrum data like the example shown in the upper plots of FIG. 4 may be the result of generating Raman spectrum data by the Raman spectrometer 114 or associated electronics, receiving the Raman spectrum data by the input interface 210 of the apparatus 200, and integrating the Raman spectrum data by the spectrum producer 252. The Raman spectrum produced by integrating the Raman spectrum data may be in various forms (not necessarily a graphical representation) for purposes of matching with known Raman spectra in the Raman database 260.

FIG. 5 is an example of SAW frequency response data and Raman spectrum data. As explained above, the SAW frequency response data samples generated by the SAW sensor 108 or associated electronics may correspond one-to-one with the Raman spectrum data samples generated by the Raman spectrometer 114 or associated electronics. For example, the SAW frequency response data and Raman spectrum data may be generated at the same sampling frequency or, if not, may be aligned with each other, trimmed, interpolated, etc. after-the-fact so as to correspond with respect to a common time dimension. Thus, as shown in FIG. 5, the data as received by the input interface 210 (or as aligned etc. by the input interface 210) may be in the form of a sample of SAW frequency response data S ($S_1$, $S_2$, . . . , $S_n$) and a sample of Raman spectrum data R ($R_1$, $R_2$, . . . , $R_n$) for each of a plurality of retention time values t ($t_1$, $t_2$, . . . , $t_n$) for n samples (e.g. 20 millisecond periods). Each of the SAW frequency response data samples $S(t_i)$ may be, for example, a value representing a change in an oscillation frequency due to the accumulation of an eluted chemical component on the SAW sensor 108 at time $t=t_i$. Each of the Raman spectrum data samples $R(t_i)$ may be, for example, a Raman spectrum sample (e.g. intensity in counts per second as a function of Raman shift in $cm^{-1}$) at time $t=t_i$. By storing the SAW frequency response data and the Raman spectrum data correlated in this manner, integration of Raman spectrum data can be defined in the SAW frequency response data domain, e.g. "from valley to valley."

Figure 6:
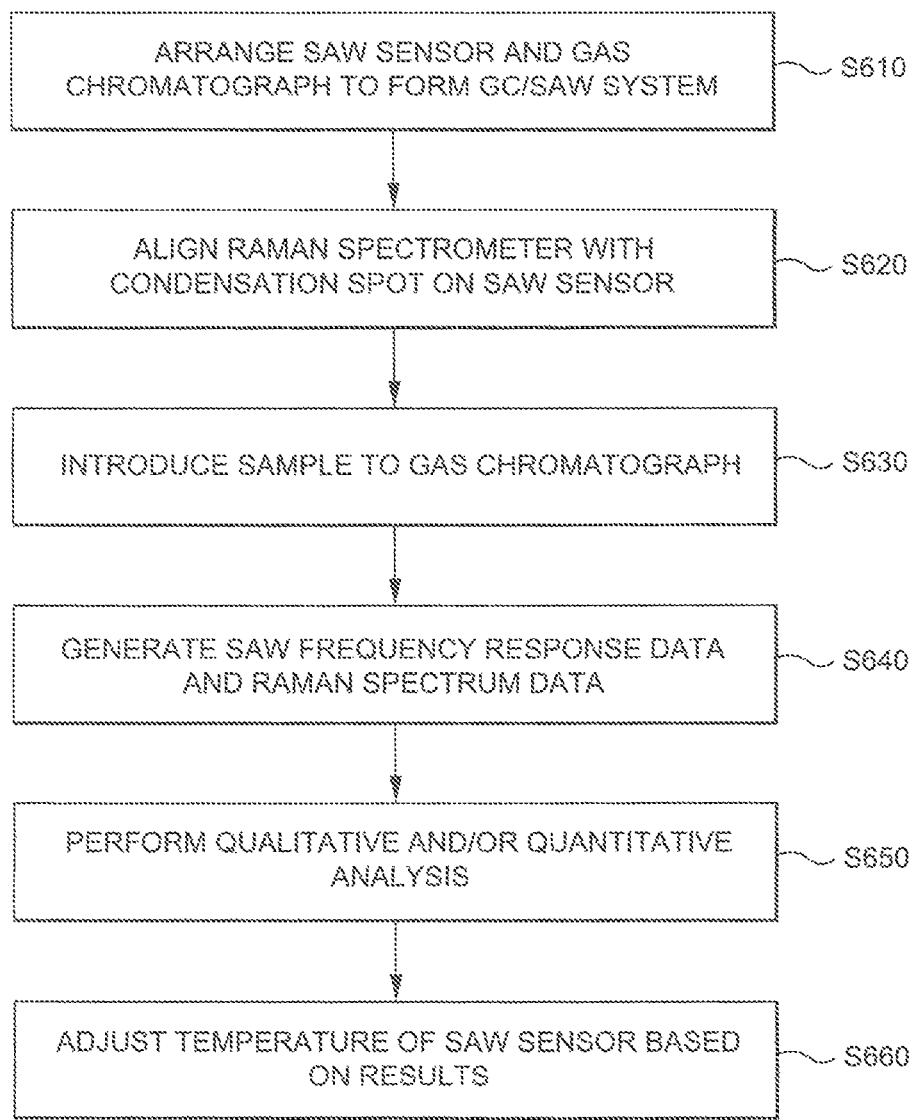
FIG. 6 shows an example operational flow in relation to the system shown in FIG. 1 according to an embodiment of the invention.

FIG. 6 shows an example operational flow in relation to the system 10 shown in FIG. 1 according to an embodiment of the invention. First, the SAW sensor 108 and the gas chromatograph 100 are arranged to form a GC/SAW system such that eluted components separated from the sample by the gas chromatograph 100 accumulate at a condensation spot 110 on the SAW sensor 108 (S610). Then, the Raman spectrometer 114 is aligned with the condensation spot 110 on the SAW sensor 108 so as to collect Raman scattered light from eluted components accumulated at the condensation spot 110 (S620). Steps S610 and 620 may, of course, be reversed or performed substantially simultaneously. Once the GC/SAW system plus Raman spectrometer 114 are set up, a sample is introduced into the gas chromatograph 100 (S630). As chemical components elute from the GC column 104, SAW frequency response data and Raman spectrum data are generated by the SAW sensor 108 and Raman spectrometer 114, respectively, or associated electronics (S640). After the SAW frequency response data and Raman spectrum data are generated, qualitative and/or quantitative analysis is performed (S650). For example, the SAW frequency response data and Raman spectrum data may be received by the apparatus 200 (e.g. transferred by a data storage medium or transferred by a wired or wireless connection, either locally or remotely) and the apparatus 200 may determine the identity of one or more chemical components of interest using the chemical evaluator 250 and/or estimate the mass or other quantitative measure of one or more chemical components of interest using the mass estimator 270. Lastly, the temperature of the SAW sensor 108 or other parameter(s) of the setup configuration of the system of FIG. 1 may be adjusted based on the results of the apparatus 200 and/or automatically by the apparatus 200 (S660).

Figure 7:
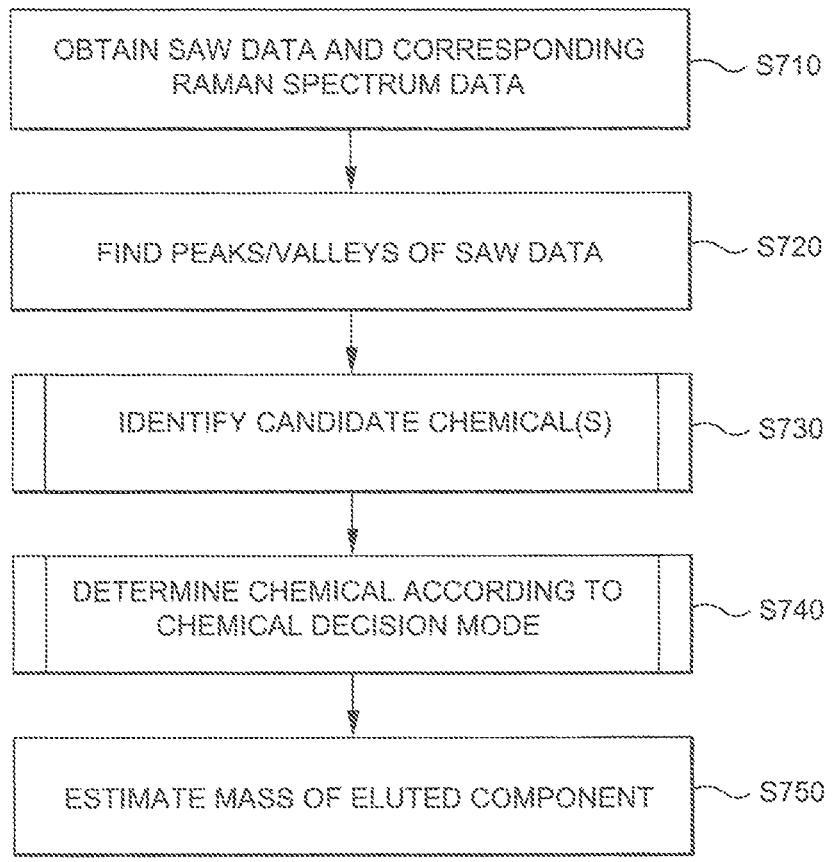
FIG. 7 shows an example operational flow of the apparatus 200 according to an embodiment of the invention.

FIG. 7 shows an example operational flow of the apparatus 200 according to an embodiment of the invention. In the example shown in FIG. 7, the apparatus 200 performs the operations from S710-S750, but the apparatus 200 shown in FIG. 2 is not limited to using this operational flow. Also, the operational flow in FIG. 7 may be performed by a modified apparatus or a different apparatus that differs from the apparatus 200 shown in FIG. 2.

First, the apparatus 200 receives SAW frequency response data and corresponding Raman spectrum data (S710). For example, the input interface 210 of the apparatus 200 may receive SAW frequency response data and corresponding Raman spectrum data generated by the SAW sensor 108 and Raman spectrometer 114 or associated electronics as described above. That is, the input interface 210 may receive SAW frequency response data generated by the SAW sensor 108 of the GC/SAW system shown in FIG. 1, the SAW frequency response data including one or more peaks corresponding respectively to one or more eluted components separated from a sample by the gas chromatograph 100, and may further receive Raman spectrum data generated by the Raman spectrometer 114 for the one or more eluted components. The input interface 210 may, as part of receiving the data, align, trim, interpolate, etc. the data so that it corresponds as shown, by way of example, in FIG. 5. The input interface 210 may reformat data from multiple sources (e.g. the SAW sensor 108 and the Raman spectrometer 114) to be in a single format for use by the apparatus 200.

Having received the SAW frequency response data and Raman spectrum data, the apparatus 200 identifies peaks and valleys of the SAW data (S720). For example, the SAW data analyzer 220 of the apparatus 200 may identify the one or more peaks of the SAW frequency response data corresponding to the eluted components and may further identify one or more valleys of the SAW frequency response data by any known method as described above. For each of the found peaks or some subset thereof, the apparatus 200 identifies a set of one or more candidate chemicals (S730). For example, the candidate chemical identifier 230 of the apparatus 200 may identify a set of one or more candidate chemicals for an eluted component of interest based on the corresponding peak of the SAW frequency response data as characterized by the SAW data analyzer 220.

With a set of one or more candidate chemicals having been identified for an eluted component of interest, the apparatus 200, e.g. the chemical evaluator 250, then determines the chemical identity of the eluted component of interest according to a selected chemical decision mode (S740). Lastly, the apparatus 200 may estimate the mass or other quantitative measure of the eluted component of interest (S750). For example, the mass estimator 270 of the apparatus 200 may estimate the mass or other quantitative measure by comparing the corresponding peak of the SAW frequency response data to a calibration curve stored in the calibration curve storage 280.

Figure 8:
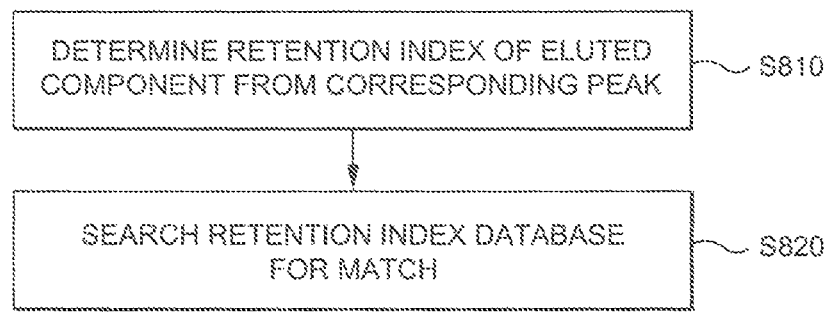
FIG. 8 is an example operational flow of step S730 in FIG. 7.

FIG. 8 is an example operational flow of step S730 in FIG. 7. For a given peak of the SAW frequency response data, the apparatus 200 may identify a set of one or more candidate chemicals using a retention index. For example, the retention index calculator 232 of the candidate chemical identifier 230 may calculate a retention index of the eluted component from the corresponding peak (S810). Then, the retention index search engine 234 may search the retention index database 240 for one or more matches between the determined retention index and chemicals in the retention index (S820). In this way, the set of one or more candidate chemicals for the peak may consist of each matched chemical in the retention index database 240, e.g. each known chemical having substantially the same retention index as the determined retention index or having retention indices within a predetermined error range of the determined retention index.

Figure 9A:
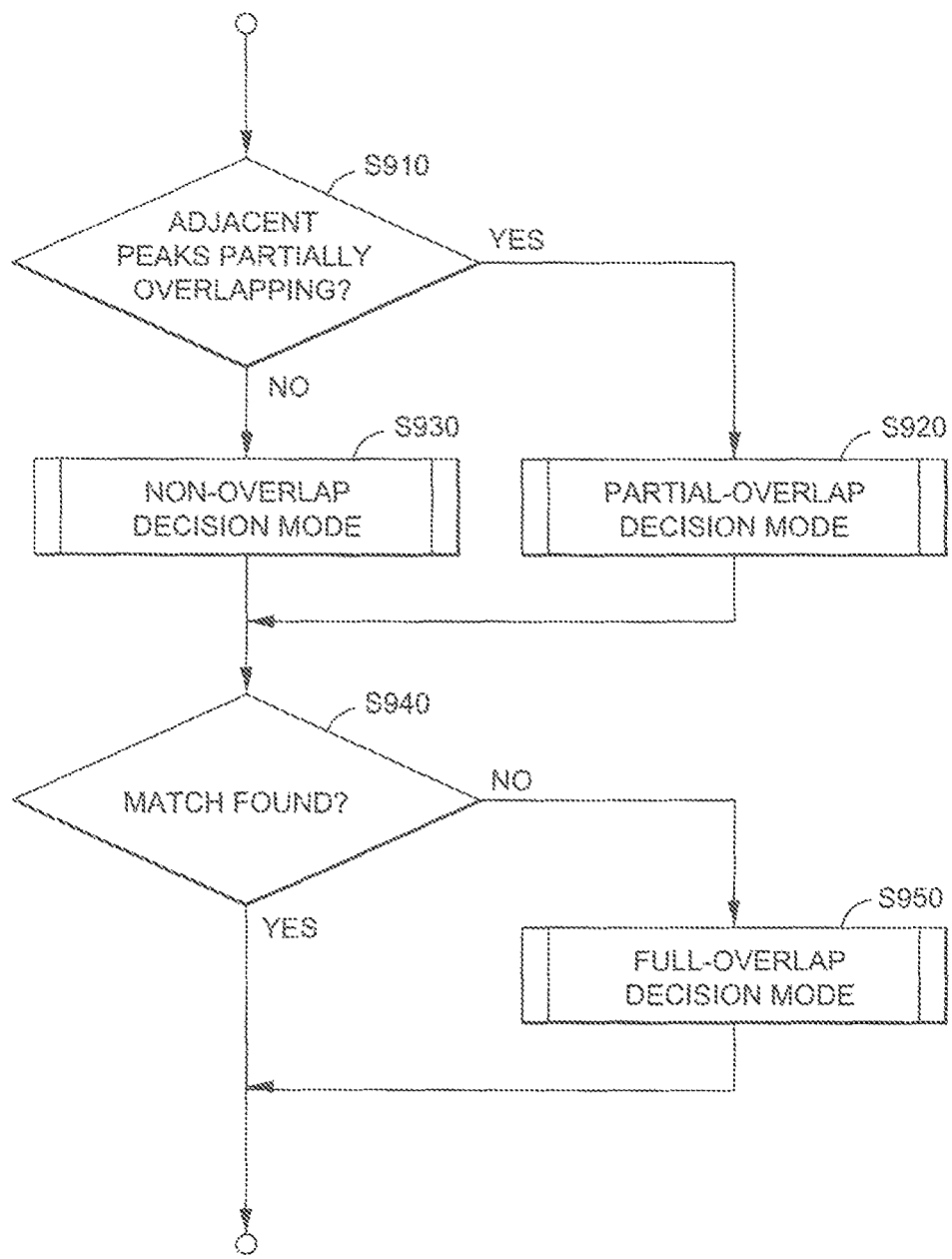
FIG. 9A is an example operational flow of step S740 in FIG. 7.

FIG. 9A is an example operational flow of step S740 in FIG. 7. First, the apparatus 200 evaluates whether adjacent peaks of the SAW frequency response data are partially overlapping (S910). For example, the SAW data analyzer 220 of the apparatus 200 may make the evaluation for every pair of adjacent peaks of the SAW frequency response data or for some subset of interest by the methodology described above. For a given set of adjacent peaks for which the evaluation is made, the SAW data analyzer 220 may characterize the adjacent peaks as being partially overlapping (e.g. mark, notate, flag, insert metadata, etc.) if it is evaluated that the adjacent peaks are partially overlapping. If it is evaluated that the adjacent peaks are not partially overlapping, the SAW data analyzer 220 may characterize the adjacent peaks as non-overlapping or leave in place a default characterization of non-overlapping.

The analyzed SAW frequency response data including the characterizations made by the SAW data analyzer 220 may then be passed to the chemical evaluator 250, which may determine the chemical identity of the component corresponding to a given peak in accordance with a selected mode. For example, for each peak belonging to a pair of adjacent peaks that the SAW data analyzer 220 characterized as partially overlapping ("Yes" at S910), the mode selector 256 of the chemical evaluator 250 may select partial-overlap decision mode and the chemical evaluator 250 may determine the identity of the chemical component according to the partial-overlap decision mode (S920). Meanwhile, for each peak not belonging to a pair of adjacent peaks that the SAW data analyzer 220 characterized as partially overlapping, or for each peak that the SAW data analyzer 220 characterized as non-overlapping or left non-overlapping by defaulting ("No" at S910), the mode selector 256 of the chemical evaluator 250 may select non-overlap decision mode (e.g. by default) and the chemical evaluator 250 may determine the identity of the chemical component according to the non-overlap decision mode (S930).

The determinations according to the partial-overlap decision mode (S920) and non-overlap decision mode (S930) may fail. That is, there are situations where the chemical evaluator 250 will not successfully determine the identity of the chemical component, such as when no match is found in the Raman database 260 for a Raman spectrum produced for the peak as described above. Some portion of these failures may be the result of the peak actually being a combination of fully overlapped peaks, which might be resolved by the full-overlap decision mode. Therefore, after the completion of step S920 or step S930, the apparatus 200, e.g. the chemical evaluator 250, may determine whether a match has been found in the Raman database 260 corresponding to each peak for which an attempt at determining the chemical identity of the component was made in step S920 or S930 (S940). For a given peak, if a match was successfully found ("Yes" at S940), the operational flow of FIG. 9A ends for that peak as the chemical has been identified. On the other hand, if a match was not successfully found ("No" at S940), the mode selector 256 of the chemical evaluator 250 may select full-overlap decision mode and the chemical evaluator 250 may determine the identity of the chemical component according to the full-overlap decision mode (S950). After attempting to determine the chemical identity of the component by the full-overlap decision mode, the operational flow of FIG. 9A ends.

Figure 9B:
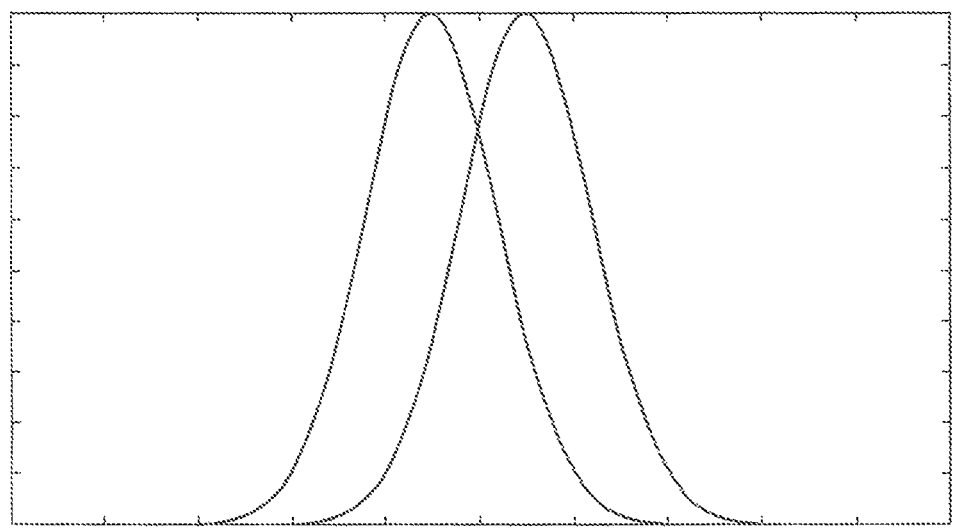
FIG. 9B is a conceptual representation of partially overlapped peaks of the SAW frequency response data.

FIG. 9B is a conceptual representation of partially overlapped peaks of the SAW frequency response data. In an exemplary GC/SAW system like the system 10 shown in FIG. 1, chemical components that elute closely in time may coexist at the condensation spot 110 for part of the time that they are condensed. For example, after a first component condenses, a second component may then condense before the first component completely evaporates. The actual SAW frequency response data in such a situation may, for example, appear as the union of the two peaks shown in FIG. 9B. In other words, the interior of the two peaks (i.e. the front of the second peak and the tail of the first peak) are not seen in the data and are only included in FIG. 9B for conceptual understanding. As described above, the SAW data analyzer 220 may characterize peaks such as those in FIG. 9B as being partially overlapped by evaluating whether the height of the valley between the peaks exceeds a valley height threshold or whether the peaks are closer together than a peak distance threshold. As can be understood from FIG. 9B, the valley between adjacent peaks may exceed a valley height threshold in a case of partially overlapping peaks because the valley does not represent an absence of condensed material on the SAW sensor 108. Rather, the valley occurs at a time when both components are accumulated on the SAW sensor 108 (the first component evaporating as the second component condenses), resulting in a significant SAW frequency response.

The exemplary representation of partially overlapped peaks is simplified in FIG. 9B, in that measured SAW frequency response data may exhibit some distortion of the peak shape in regions of overlap. The accumulation of the mass of the second component may inflate the apparent mass of the first component, and vice versa, and may, in some cases, even shift the first and second peaks. An error range for identifying a set of candidate chemicals for each peak, e.g., an error range when looking up a determined retention index in the retention index database 240, may help avoid complications caused by distortions of this kind.

Figure 9C:
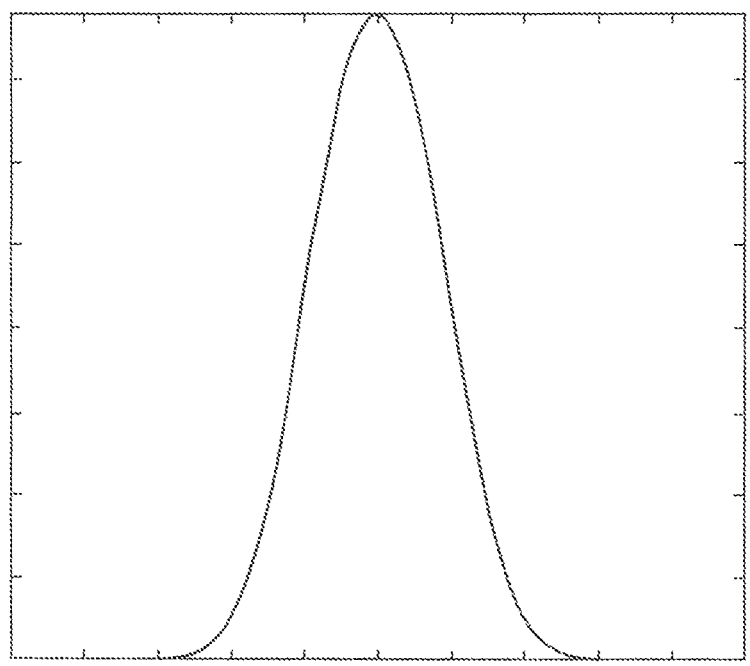
FIG. 9C is a conceptual representation of fully overlapped peaks of the SAW frequency response data.

FIG. 9C is a conceptual representation of fully overlapped peaks of the SAW frequency response data. In an exemplary GC/SAW system like the system 10 shown in FIG. 1, chemical components that elute closely in time may coexist at the condensation spot 110 for a long enough duration of the time they are condensed that no valley is detected between the peaks. The actual SAW frequency response data in such a situation may appear as the single peak shown in FIG. 9C, which may be indistinguishable from a single peak resulting from a single eluted component. As described above, the SAW data analyzer 220 may characterize peaks such as those in FIG. 9C as not being partially overlapped, or as being non-overlapped, by evaluating whether the height of the valley between the apparently single peak and an adjacent peak (not shown) exceeds a valley height threshold or whether the apparently single peak is closer to an adjacent peak than a peak distance threshold. In this case, there is no peak near the apparently single peak of FIG. 9C, so the SAW data analyzer 220 may characterize the apparently single peak as not partially overlapped or as non-overlapped (or leave the peak uncharacterized to be interpreted as non-overlapped by default).

As noted above, the overlapping of peaks may distort the shape of the peaks as the accumulation of the mass of the second component inflates the apparent mass of the first component, and vice versa. The closer the peaks are together, the more likely this effect will eliminate any valley between the peaks, as the combined mass of both chemical components results in a greater SAW frequency response than that of either of the two peaks. Since there is no valley in this situation, the result is fully overlapped peaks as shown in FIG. 9C, though the apparently single peak may have a distorted shape. The error range for identifying a set of candidate chemicals for each peak, e.g. the error range when looking up a determined retention index in the retention index database 240, may be set to be wide enough so that the chemicals of the adjacently eluted components are included in the set of candidate chemicals returned by the candidate chemical identifier 230 for the single distorted peak.

Figure 9D:
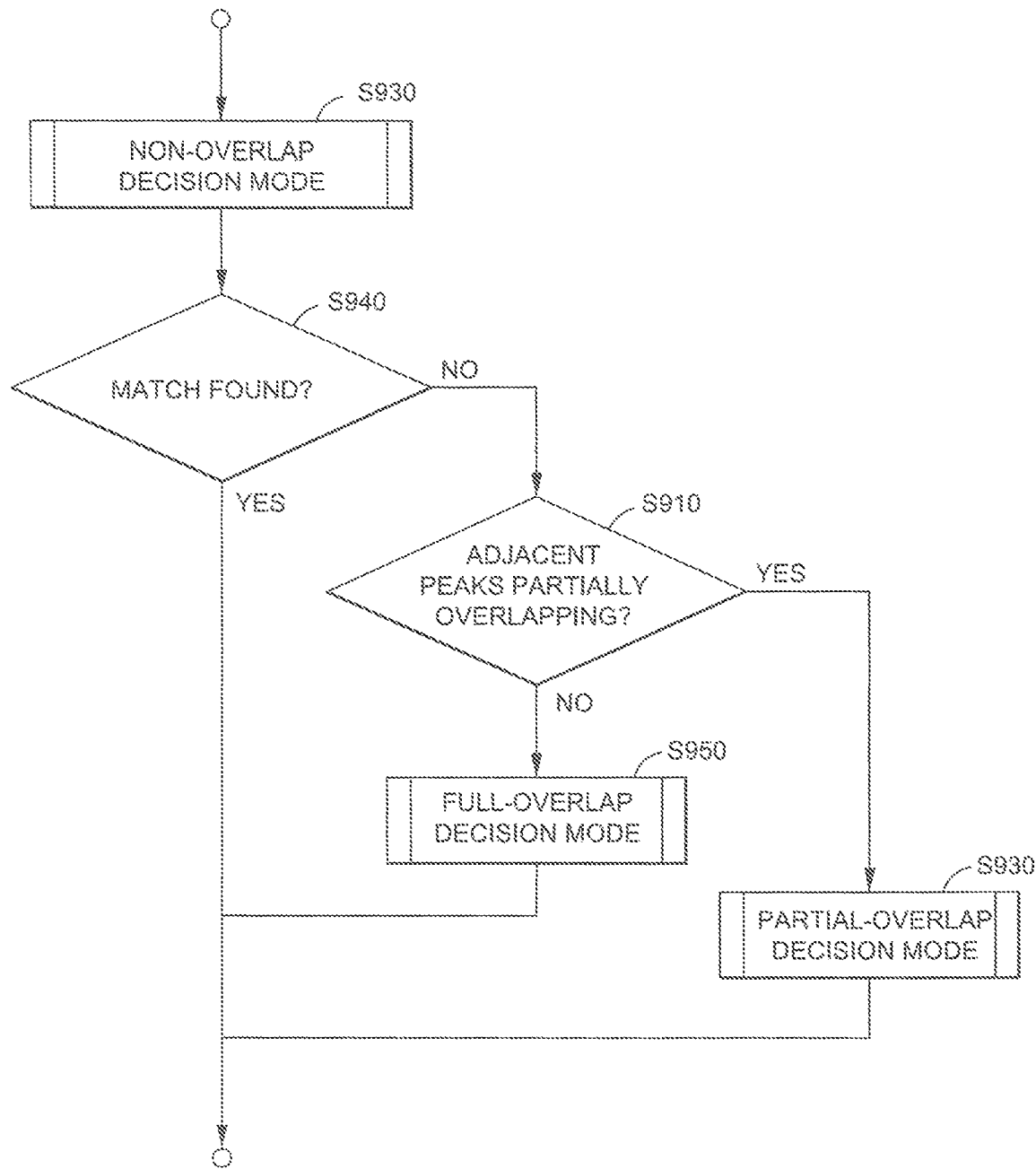
FIG. 9D is another example operational flow of step S740 in FIG. 7.

FIG. 9D is another example operational flow of step S740 in FIG. 7. In the example of FIG. 9D, the order of steps S910 and S940 are reversed. That is, it is first evaluated whether a match has been found in the Raman database 260 corresponding to each peak (S940), and thereafter it is evaluated whether adjacent peaks of the SAW frequency response data are overlapping (S910). As noted above, one of the reasons for evaluating whether adjacent peaks are partially overlapped peaks is that such peaks may be so close together that accurate Raman spectra of the chemical components may be difficult to produce. Thus, if the SAW data analyzer 220 does not seek partially overlapped peaks, it is likely that the chemical evaluator 250 will not find Raman matches for those peaks that are too close together (i.e. the peaks that should have been characterized as partially overlapped peaks). More specifically, the spectrum producer 252 may still produce a Raman spectrum by integrating valley-to-valley for each peak in accordance with the non-overlap decision mode, but the Raman search engine 254 will likely not find matches in the Raman database 260 because the produced Raman spectra will be too distorted by the adjacent chemical component. On the other hand, depending on the threshold(s) for evaluating adjacent peaks as partially overlapping, there may be cases where matches could have been found and partial-overlap decision mode (described in more detail below) was unnecessary. The operational flow of FIG. 9D may skip this initial evaluation of partially overlapped peaks by the SAW data analyzer 220 and instead initially assumes that all peaks are non-overlapping.

Specifically, the operational flow of FIG. 9D begins with the chemical evaluator 250 determining the identity of each chemical component of interest according to the non-overlap decision mode (S930). Then, the chemical evaluator 250 may evaluate whether a match has been found in the Raman database 260 corresponding to each peak for which an attempt at determining the chemical identity of the component was made in step S930 (S940). For a given peak, if a match was successfully found ("Yes" at S940), the operational flow of FIG. 9D ends for that peak as the chemical has been identified. If, on the other hand, a match was not successfully found ("No" at S940), the apparatus 200 (e.g. the SAW data analyzer 220) may then evaluate whether the unmatched peak belongs to a pair of adjacent peaks of the SAW frequency response data that are partially overlapping (S910). For each peak belonging to a pair of adjacent peaks that the SAW data analyzer 220 characterized as partially overlapping ("Yes" at S910), the mode selector 356 of the chemical evaluator 250 may select partial-overlap decision mode and the chemical evaluator 250 may determine the identity of the chemical component according to the partial-overlap decision mode (S920). Meanwhile, for each peak not belonging to a pair of adjacent peaks that the SAW data analyzer 220 characterized as partially overlapping ("No" at S910), the mode selector 256 of the chemical evaluator 250 may select full-overlap decision mode and the chemical evaluator 250 may determine the identity of the chemical component according to the full-overlap decision mode (S950). After attempting to determine the chemical identity of the component by the partial-overlap decision mode or the full-overlap decision mode, the operational flow of FIG. 9D ends.

In addition to FIGS. 9A and 9D, there may be other operational flows by which the chemical decision modes can be selected and implemented in step S740 of FIG. 7. For instance, considering the possibility of fully overlapping peaks within a pair of partially overlapping peaks, the operational flow may be modified to loop back and repeat or combine multiple chemical decision modes as the situation may demand or in accordance with a tradeoff between accuracy and efficiency. Also, the operational flow of step S740 may further include a final evaluation of whether a match was found for a given peak. This information may be used, e.g. by the output interface 290 as part of the output of the apparatus 200. For example, match successes and failures may contain useful information for purposes of error reporting or adjusting of the setup parameters of the system components as described above (including adjusting the temperature of the SAW sensor 108 using the thermoelectric cooler 112).

Figure 10:
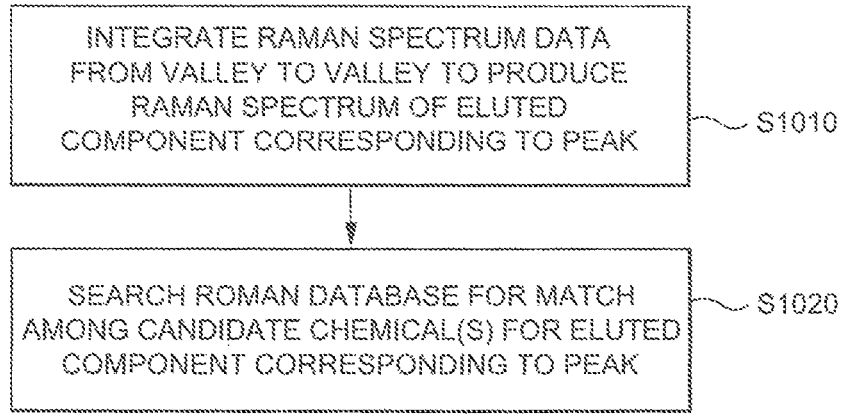
FIG. 10 is an example operational flow of step S930 in FIGS. 9A and 9D.

FIG. 10 is an example operational flow of step S930 in FIGS. 9A and 9D. That is, FIG. 10 is an example of determining the chemical identity of an eluted component of interest in accordance with the non-overlap decision mode, e.g. upon selection of the non-overlap decision mode for a given peak by the mode selector 256. First, the spectrum producer 252 may integrate the Raman spectrum data from valley to valley, i.e. from a valley immediately preceding the peak corresponding to the eluted component of interest to a valley immediately following the peak corresponding to the eluted component of interest (S1010). Then, the Raman search engine 254 searches the Raman database 260 for a match between the Raman spectrum produced by the spectrum producer 252 and a chemical in the Raman database 260 from among the set of candidate chemicals for the eluted component of interest (S1020).

Figure 11A:
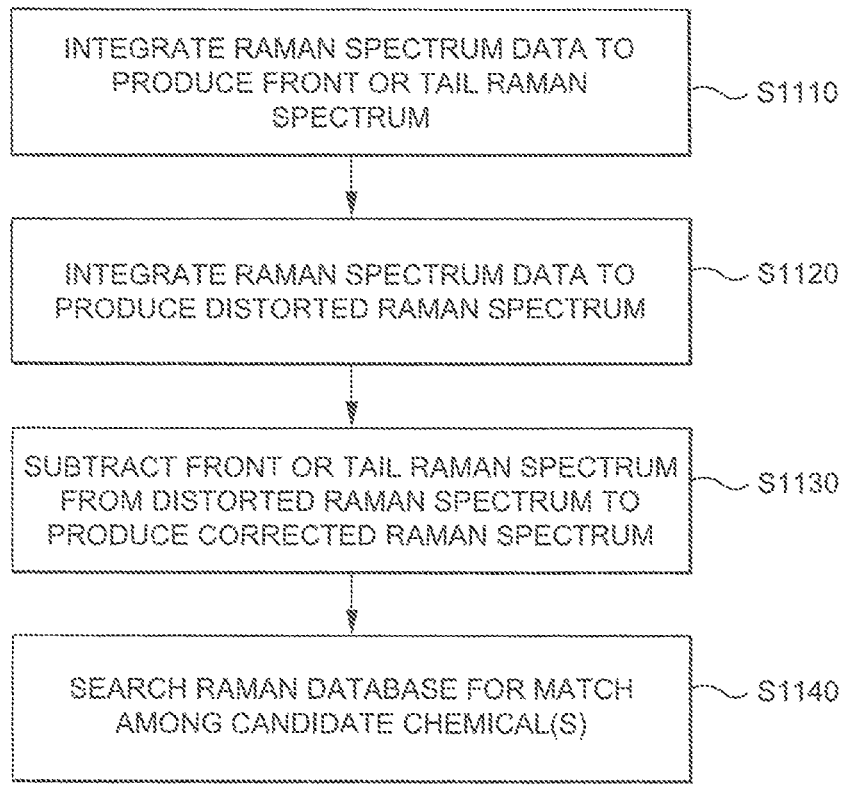
FIG. 11A is an example operational flow of step S920 in FIGS. 9A and 9D.

FIG. 11A is an example operational flow of step S920 in FIGS. 9A and 9D. That is, FIG. 11 is an example of determining the chemical identity of an eluted component of interest in accordance with the partial-overlap decision mode, e.g. upon selection of the partial-overlap decision mode for a given pair of adjacent peaks by the mode selector 256. First, the spectrum producer 252 integrates the Raman spectrum data to produce a front or tail Raman spectrum (S1110). Specifically, the spectrum producer 252 may integrate the Raman spectrum data from a valley immediately preceding the first of the adjacent peaks to a point prior to a valley between the adjacent peaks, thereby producing a front Raman spectrum of the first of the adjacent peaks. Alternatively, the spectrum producer 252 may integrate the Raman spectrum data from a point after the valley between the adjacent peaks to a valley immediately following the second of the adjacent peaks, thereby producing a tail Raman spectrum of the second of the adjacent peaks. With reference to FIG. 9B, the point prior to the valley between the adjacent peaks may be any point to the left of the valley between the peaks (but still within the first peak). Likewise, the point after the valley between the adjacent peaks may be any point to the right of the valley between the peaks (but still within the second peak). Thus, unlike the non-overlap decision mode, where integration of the first peak would be from valley to valley (i.e. all the way to the valley between the peaks), the partial-overlap decision mode involves the spectrum producer 252 integrating only a front of the first peak to produce a front Raman spectrum. Likewise, unlike the non-overlap decision mode, where integration of the second peak would be from valley to valley (i.e. beginning at the valley between the peaks), the partial-overlap decision mode involves the spectrum producer 252 integrating only a tail of the second peak to produce a tail Raman spectrum.

The point prior to the valley between the adjacent peaks and/or the point after the valley between the adjacent peaks may be selected based on, for example, a predetermined front/tail length, a predetermined distance from the valley between the peaks, a predetermined fraction or percentage of the peak, etc. The selection criteria may depend on the distance between the peaks or the height of the valley between the peaks, as determined by the SAW data analyzer 220 when evaluating whether the peaks are partially overlapping. For example, it may be necessary to use a smaller front or tail for peaks that are more overlapped. The selection of the point may depend on many other factors, such as the signal-to-noise ratio, the integration time needed to produce a Raman spectrum, the condensation time or temperature of the SAW sensor 108, etc. It is contemplated that the point prior to the valley and the point after the valley, and/or the selection criteria, may be adjusted by a user and/or adjusted automatically by the apparatus 200 based on any combination of relevant factors, with the goal being to produce a front or tail Raman spectrum by which a match can be found. An iterative approach (e.g. iterated automatically) is also possible, where larger and larger or smaller and smaller front/tail Raman spectra are generated until a Raman match is found.

With a front Raman spectrum of the first peak or a tail Raman spectrum of the second peak having been produced in step S1110, the spectrum producer 252 then (before, after, or concurrently with step S1110) integrates the Raman spectrum data of the other peak from valley to valley, thus producing a distorted Raman spectrum of the other peak (S1120). For example, in a case where a front Raman spectrum of the first peak is produced in step S1110, the spectrum producer 252 may integrate the Raman spectrum data from the valley between the adjacent peaks to the valley immediately following the second of the adjacent peaks, thereby producing a distorted Raman spectrum of the second of the adjacent peaks. Or, in a case where a tail Raman spectrum of the second peak is produced in step S1110, the spectrum producer may integrate the Raman spectrum data from the valley immediately preceding the first of the adjacent peaks to the valley between the adjacent peaks, thereby producing a distorted Raman spectrum of the first of the adjacent peaks. Such Raman spectra are referred to as "distorted" because, due to the partially overlapping nature of the peaks, they are likely to suffer significant influence from the nearby peak making a direct Raman match of the distorted Raman spectrum difficult.

Thus, at the end of step S1120, the spectrum producer 252 has produced either a front Raman spectrum of the first peak and a distorted Raman spectrum of the second peak, or a tail Raman spectrum of the second peak and a distorted Raman spectrum of the first peak. Next, the spectrum producer 252 may subtract the front or tail Raman spectrum from the distorted Raman spectrum, thereby producing a corrected Raman spectrum (S1130). For example, in the case where the spectrum producer 252 has produced a front Raman spectrum of the first peak and a distorted Raman spectrum of the second peak, the spectrum producer 252 may subtract the produced front Raman spectrum of the first peak from the distorted Raman spectrum of the second peak, thereby producing a corrected Raman spectrum of the second peak. Or, in the case where the spectrum producer 252 has produced a tail Raman spectrum of the second peak and a distorted Raman spectrum of the first peak, the spectrum producer 252 may subtract the produced tail Raman spectrum of the second peak from the distorted Raman spectrum of the first peak, thereby producing a corrected Raman spectrum of the first peak.

Lastly, with sets of candidate chemicals for the eluted components corresponding to the first and second peaks having been identified by the candidate chemical identifier 230, the Raman search engine 254 searches the Raman database 260 for matches among the candidate chemicals(s) using the front/tail and/or corrected Raman spectra (S1140). For example, in a case where the spectrum producer 252 has produced a front Raman spectrum of the first peak and a corrected Raman spectrum of the second peak, the Raman search engine 254 may search the Raman database 260 for a match between the produced front Raman spectrum and a chemical in the Raman database 260 from among the set of candidate chemicals for the eluted component corresponding to the first of the adjacent peaks. Instead, or additionally (depending on which peak or peaks are of interest), the Raman search engine 254 may search the Raman database 260 for a match between the corrected Raman spectrum of the second of the adjacent peaks and a chemical in the Raman database 260 from among the set of candidate chemicals for the eluted component corresponding to the second of the adjacent peaks. On the other hand, in a case where the spectrum producer 252 has produced a tail Raman spectrum of the second peak and a corrected Raman spectrum of the first peak, the Raman search engine 254 may search the Raman database 260 for a match between the produced tail Raman spectrum and a chemical in the Raman database 260 from among the set of candidate chemicals for the eluted component corresponding to the second of the adjacent peaks. Instead, or additionally (depending on which peak or peaks are of interest), the Raman search engine 254 may search the Raman database 260 for a match between the corrected Raman spectrum of the first of the adjacent peaks and a chemical in the Raman database 260 from among the set of candidate chemicals for the eluted component corresponding to the first of the adjacent peaks. In this way, the partially overlapping peaks may be effectively separated and the chemical component corresponding to one or both peaks may be identified.

Figure 11B:
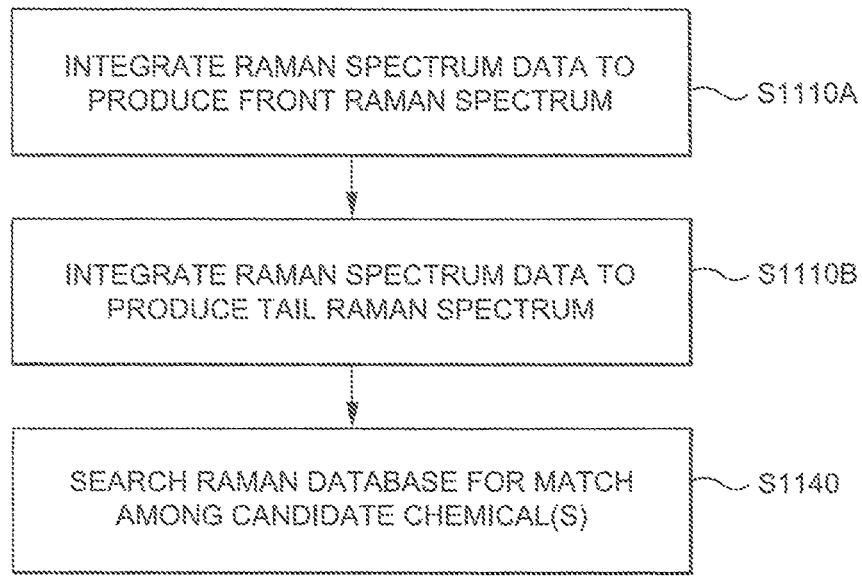
FIG. 11B is another example operational flow of step S920 in FIGS. 9A and 9D.

FIG. 11B is another example operational flow of step S920 in FIGS. 9A and 9D. In the example of FIG. 11B, the spectrum producer 252 does not produce a corrected spectrum but instead produces both a front spectrum of the first peak and a tail spectrum of the second peak. First, the spectrum producer 252 integrates the Raman spectrum data to produce a front Raman spectrum of the first peak (S1110A). Specifically, the spectrum producer 252 may integrate the Raman spectrum data from a valley immediately preceding the first of the adjacent peaks to a point prior to a valley between the adjacent peaks, thereby producing a front Raman spectrum of the first of the adjacent peaks. Then (before, after, or concurrently with step S1110A), the spectrum producer 252 integrates the Raman spectrum data to produce a tail Raman spectrum of the second peak (S1110B). Specifically, the spectrum producer 252 may integrate the Raman spectrum data from a point after the valley between the adjacent peaks to a valley immediately following the second of the adjacent peaks, thereby producing a tail Raman spectrum of the second of the adjacent peaks. Lastly, with sets of candidate chemicals for the eluted components corresponding to the first and second peaks having been identified by the candidate chemical identifier 230, the Raman search engine 254 searches the Raman database 260 for matches among the candidate chemicals(s) using the front and/or tail Raman spectra (S1140). For example, the Raman search engine 254 may search the Raman database 260 for a match between the produced front Raman spectrum and a chemical in the Raman database 260 from among the set of candidate chemicals for the eluted component corresponding to the first of the adjacent peaks. Instead, or additionally (depending on which peak or peaks are of interest), the Raman search engine 254 may search the Raman database 260 for a match between the produced tail Raman spectrum and a chemical in the Raman database 260 from among the set of candidate chemicals for the eluted component corresponding to the second of the adjacent peaks. In this way as well, the partially overlapping peaks may be effectively separated and the chemical component corresponding to one or both peaks may be identified.

Figure 12:
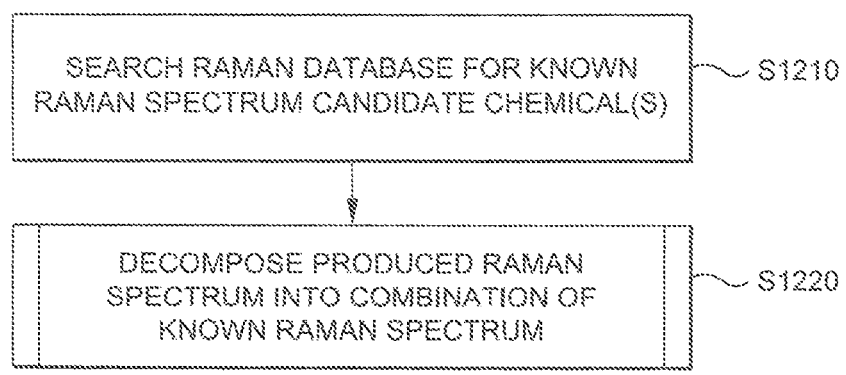
FIG. 12 is an example operational flow of step S950 in FIGS. 9A and 9D.

FIG. 12 is an example operational flow of step S950 in FIGS. 9A and 9D. That is, FIG. 12 is an example of determining the chemical identity of an eluted component of interest in accordance with the full-overlap decision mode, e.g. upon selection of the full-overlap decision mode for a given peak by the mode selector 256. As discussed above, the full-overlap decision mode may be selected, for example, when a Raman match is not found using another decision mode. In the non-overlap decision mode and partial-overlap decision mode, Raman searches by the Raman search engine 254 are conducted to find a chemical for a given Raman spectrum that has been produced. In the full-overlap decision mode, the Raman search is conducted "in reverse," that is, to find a Raman spectrum for a given chemical that has been identified as a candidate chemical by the candidate chemical identifier 230.

First, with a set of candidate chemicals for the apparently single peak (actually more than one fully-overlapped peaks) having been identified by the candidate chemical identifier 230, the Raman search engine 254 searches the Raman database 260 for known Raman spectra of the one or more candidate chemicals (S1210). It should be noted that, for purposes of the full-overlap mode, it can be assumed that the one or more candidate chemicals returned by the candidate chemical identifier 230 may include at least two candidate chemicals. If there were only one candidate chemical, it may be assumed that the apparently single peak is not a combination of fully-overlapped peaks and bypass the full-overlap mode. Since the candidate chemicals for the peak are those chemicals identified for the retention time of the peak (e.g. chemicals having the same or similar retention index as determined from the peak), the set of returned known Raman spectra is understood to include the Raman spectra of the actual eluted components that combined to produce the peak. In other words, the fully-overlapped peaks, if separable, may be understood to produce Raman spectra from the set of returned known Raman spectra. Thus, the goal is to find the subset of the returned known Raman spectra that represent the actual eluted components that combined to produce the peak.

To achieve the above goal, the spectrum producer 252 decomposes a Raman spectrum produced for the peak into a combination of the known Raman spectra returned by the Raman search engine 254 (S1220). As described earlier (see e.g. FIG. 9A), the spectrum producer 252 is understood to have produced a Raman spectrum for the peak in accordance with a previously selected mode. This may be, for example, a valley-to-valley Raman spectrum produced in accordance with the non-overlap mode, a corrected Raman spectrum produced in accordance with the partial-overlap mode, or a front/tail Raman spectrum produced in accordance with the partial-overlap mode. In any case, a match with the produced Raman spectrum has not been found, thereby resulting in the selection of full-overlap mode. Alternatively, the full-overlap mode itself may include the spectrum producer 252 producing a valley-to-valley Raman spectrum of the apparent single peak. The produced Raman spectrum, whenever and however it is produced, may be decomposed into a combination of the known Raman spectra by any known method, such as by a self-modeling mixture analysis method, a self-modeling curve resolution method, a systematic trial-and-error routine of subtracting the known Raman spectra from the produced Raman spectrum, or a computational method. By decomposing the produced Raman spectrum into the known Raman spectra corresponding to the candidate chemicals, the chemical evaluator 250 may deduce the chemical identity of the eluted components that combined to result in the produced Raman spectrum for that retention time. If, on the other hand, it is not possible to decompose the produced Raman spectrum into the known Raman spectra, full-overlap mode fails. There may be some other problem with the system as described above.

Figure 13:
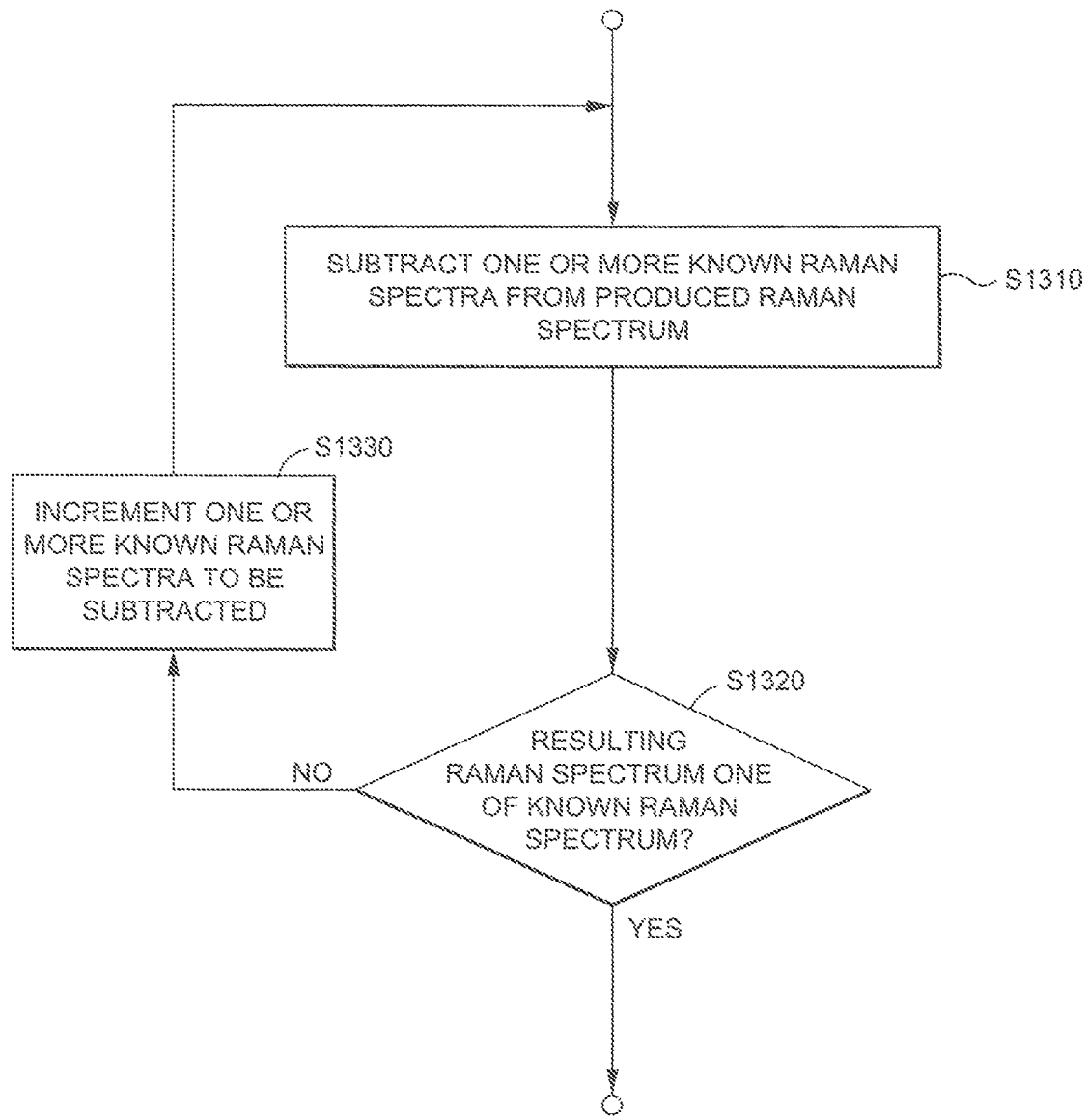
FIG. 13 is an example operational flow of step S1220 in FIG. 12.

FIG. 13 is an example operational flow of step S1220 in FIG. 12. First, the spectrum producer 252 subtracts one or more of the known Raman spectra found in step S1210 of FIG. 12 from the Raman spectrum produced for the peak by the spectrum producer 252 (e.g. the Raman spectrum produced by integrating valley to valley in the non-overlap mode) (S1320). The spectrum producer 252 then validates that the Raman spectrum resulting from the subtraction is itself one of the known Raman spectra found in step S1210 of FIG. 12 (S1320). If the resulting Raman spectrum is one of the known Raman spectra ("Yes" at S1320), then the decomposing is understood to have been successful, and it may be concluded that the Raman spectrum produced by the spectrum producer 252 (for which there was no match) is a combination of the known spectra that were subtracted from the produced Raman spectrum in step S1310 and the resulting Raman spectrum that was validated in step S1320. The validation may be performed by matching the Raman spectrum resulting from the subtraction with each of the remaining known Raman spectra. Matching can be achieved, for example, in the same way as matching to spectra in the Raman database 260, e.g. such that a difference between the Raman spectrum resulting from the subtraction and the known Raman spectrum is within a predetermined range.

If, on the other hand, the validation fails ("No" at step S1320), the spectrum producer 252 repeats the process using a different one or more of the known Raman spectra in the next iteration of step S1310. That is, the spectrum producer 252 increments the one or more known Raman spectra to be subtracted (S1330). For example, if the known Raman spectra consist of known Raman spectra $R_{known\_}1$, $R_{known\_}2$, $R_{known\_}3$, $R_{known\_}4$, and $R_{known\_}5$, the first iteration of step S1310 may be to subtract $R_{known\_}1$ from the produced Raman spectrum. After validation fails at step S1320, the spectrum producer 252 may then increment to $R_{known\_}2$ at step S1330 and subtract $R_{known\_}2$ from the produced Raman spectrum at the next iteration of step S1310. Assuming validation fails for $R_{known\_}1$, $R_{known\_}2$, $R_{known\_}3$, $R_{known\_}4$, and $R_{known\_}5$ in this way, the spectrum producer 252 may then increment to the combination of $R_{known\_}1$ and $R_{known\_}2$ at step S1330. That is, in the sixth iteration of step S1310, the spectrum producer 252 may subtract both $R_{known\_}1$ and $R_{known\_}2$ from the produced Raman spectrum. The pattern of incrementing may continue with subtracting $R_{known\_}1$ and $R_{known\_}3$, subtracting $R_{known\_}1$ and $R_{known\_}4$, subtracting $R_{known\_}1$ and $R_{known\_}5$, subtracting $R_{known\_}2$ and $R_{known\_}3$, subtracting $R_{known\_}2$ and $R_{known\_}4$, subtracting $R_{known\_}2$ and $R_{known\_}5$, etc., eventually including combinations of three or more known Raman spectra. At any time, if validation succeeds at step S1320, the loop ends because a validated combination of the known Raman spectra is found. For instance, if the subtraction of the combination of $R_{known\_}2$ and $R_{known\_}4$ at step S1310 yields $R_{known\_}5$ as the resulting Raman spectrum at step S1320, it is understood to mean that the resulting Raman spectrum was one of the known Raman spectra ("Yes" at S1320). The spectrum producer may thus conclude that the produced Raman spectrum (for which there was no match) is a combination of $R_{known\_}2$, $R_{known\_}4$, and $R_{known\_}5$, all of which are known Raman spectra for chemicals from among the set of candidate chemicals identified by the candidate chemical identifier 230.

In this way, the spectrum producer 252 may decompose the Raman spectrum produced for a peak of interest into a set of known Raman spectra corresponding to candidate chemicals of the peak. The chemical identity of the combination of eluted components corresponding to the peak may thus be identified by the chemical evaluator 250. The operational flow of FIG. 13 represents one of many possible routines for decomposing the produced Raman spectrum and is simplified for ease of explanation. In practice, the simple subtraction routine of FIG. 13 may be a weighted decomposition, where each of the subtracted known Raman spectra is also weighted by some multiplier, and can be solved by known computational methods. That is, the task of decomposing the produced Raman spectrum into a combination of $R_{known\_}1$, $R_{known\_}2$, $R_{known\_}3$, $R_{known\_}4$, and $R_{known\_}5$ may be implemented as a mathematical process of finding weight coefficients $w_1$, $w_2$, $w_3$, $w_4$, and $w_5$ for the expression $w_1 R_{known\_}1 + w_2 R_{known\_}2 + w_3 R_{known\_}3 + w_4 R_{known\_}4 + w_5 R_{known\_}5 = R_{produced}$, where $R_{produced}$ is the spectrum originally produced by the spectrum producer 252 that did not have a match in the Raman database 260.

It should be noted that, in the case of fully overlapped peaks, it may not be possible to estimate the mass or other quantitative measure directly from the SAW frequency response data as described above (e.g. comparing the peak to a calibration curve). However, quantitative analysis can still be achieved by taking into consideration the set of known Raman spectra that resulted from the decomposition by the spectrum producer 252 in step S1220 of FIG. 12. In particular, the weight ratio of the known Raman spectra that compose the originally produced Raman spectrum can be used to more accurately estimate the mass or other quantitative measure. For example, if the apparently single peak (combination of fully overlapped peaks) is the result of a combination of eluted chemical components having known Raman spectra $R_{known\_}2$, $R_{known\_}4$, and $R_{known\_}5$ as in the above example, with $w_1=0$, $w_2=1$, $w_3=0$, $w_4=1.2$, and $w_5=2.9$, the ratio of weights $w_2=1$, $w_4=1.2$, and $w_5=2.9$ can be applied to the original peak of the SAW frequency response data by the mass determining section 270 before consulting the calibration curve storage 280. In this way, the estimated peak area or peak height proportionately attributable to each chemical component can be used to determine the mass or other quantitative measure. Similar techniques can be used to improve the quantitative analysis for partially overlapping peaks in some cases.

In the examples described above with respect to the apparatus 200, a set of candidate chemicals is identified by GC/SAW retention index matching to narrow down the Raman search, with the Raman search being conducted within the set of candidate chemicals. However, the present disclosure is not limited to this procedure and other procedures may be used with the system 10 shown in FIG. 1 as well as with the apparatus 200. For example, the Raman search may instead be used to narrow down the GC/SAW retention index matching. The qualitative method that is used as the "coarse" identifier may be performed with appropriately large error thresholds to allow multiple candidate matches, while the qualitative method that is used as the "fine" identifier may be performed with smaller error thresholds to find a single result. Or, rather than using one qualitative analysis method to narrow down the other, two competing qualitative analyses can be conducted by GC/SAW retention index matching and Raman spectrum matching, with the chemical identity of each component being determined by statistical methods.

By using the systems, methods, and apparatuses described herein, it is possible to identify trace amounts of chemicals, e.g. nanogram chemicals in a complex sample matrix with limited separation power because the identification is based on information from the entire molecular structure instead of fragment information as in the case of gas chromatography/mass spectrometry (GC/MS) systems. For conventional GC systems, including GC/MS, accurate identification requires very good separation to avoid overlaps of peaks. The additional identification by MS is based on recombination of fragments produced by the target molecules and the additional fragments from different chemicals may introduce information that is not from signal compounds but from multiple chemicals. Because the systems, methods, and apparatuses described herein can accurately identify chemicals even when they are overlapped, the requirements of the GC/SAW system can be relaxed, with the size of the instrument and cost of operation being reduced accordingly.

Figure 14A:
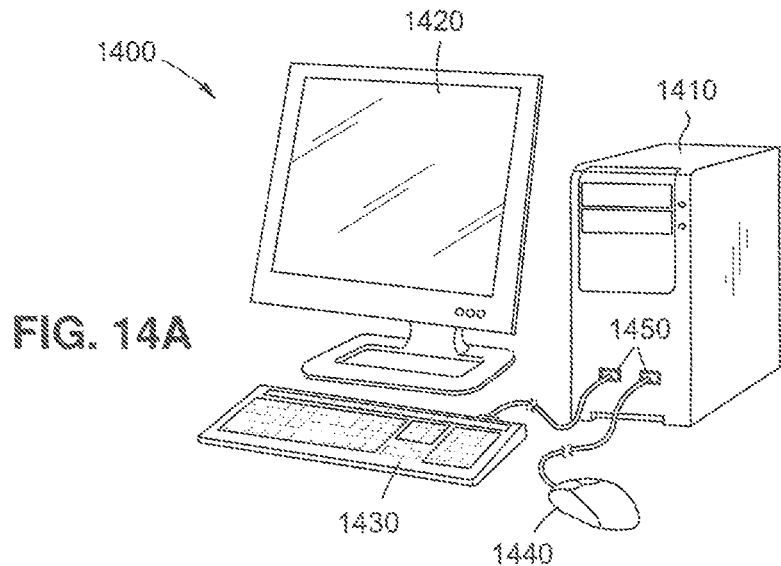
FIGS. 14A and 14B show an example of a computer 1400 in which the apparatus 200 of FIG. 2, the operational flows of FIGS. 6-13, and/or other embodiments of the claimed invention may be wholly or partly embodied, with FIG. 14A showing a computer 1400 and FIG. 14B showing a block diagram of a system unit 1410.
Figure 14B:
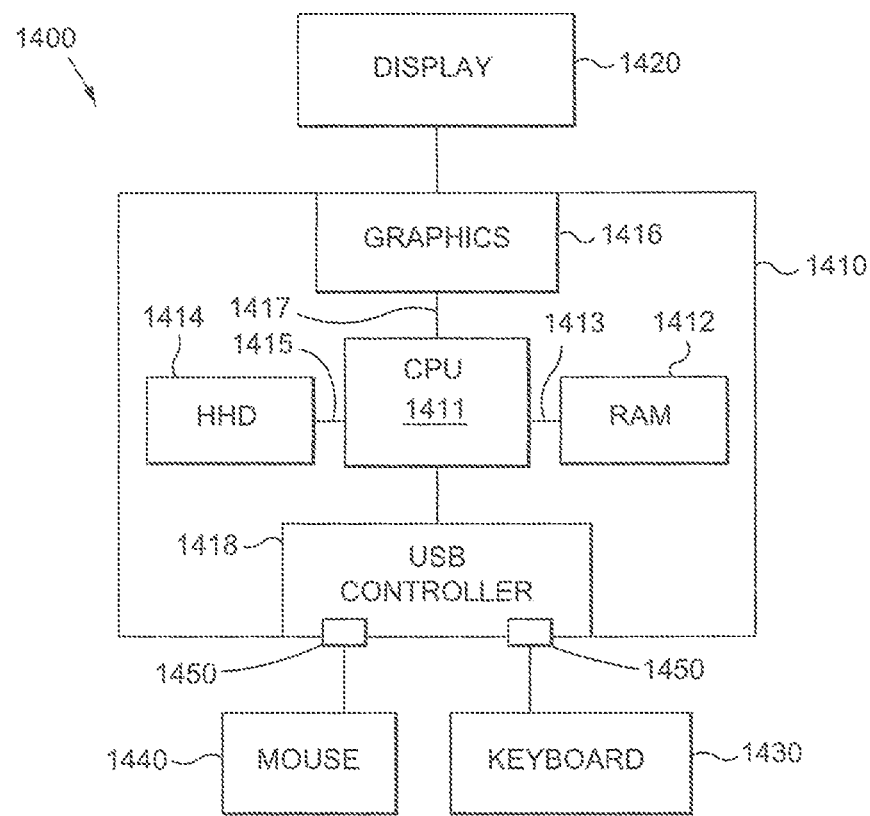

FIGS. 14A and 14B show an example of a computer 1400 in which the apparatus 200 of FIG. 2, the operational flows of FIGS. 6-13, and/or other embodiments of the claimed invention may be wholly or partly embodied. The computer 1400 according to the present embodiment, as shown in FIG. 14A, generally includes a system unit 1410 and a display device 1420. The display device 1420 produces a graphical output from the data processing operations performed by the system unit 1410. Input devices including a keyboard 1430 and a mouse 1440, for example, may be manipulated by a user to generate corresponding inputs to the data processing operations, and are connected to the system unit 1410 via ports 1450. Various other input and output devices may be connected to the system unit 1410, and different interconnection modalities are known in the art.

As shown in the block diagram of FIG. 14B, the system unit 1410 includes a processor (CPU) 1411, which may be any conventional type. A system memory (RAM) 1412 temporarily stores results of the data processing operations performed by the CPU 1411, and is interconnected thereto typically via a dedicated memory channel 1413. The system unit 1410 may also include permanent storage devices such as a hard drive 1414, which is also in communication with the CPU 1411 over an input/output (I/O) bus 1415. A dedicated graphics module 1416 may also connected to the CPU 1411 via a video bus 1417, and transmits signals representative of display data to the display device 1420. As indicated above, the keyboard 1430 and the mouse 1440 are connected to the system unit 1410 over the ports 1450. In embodiments where the ports 1450 are Universal Serial Bus (USB) type, there may be a USB controller 1418 that translates data and instructions to and from the CPU 1411 for the external peripherals connected via the ports 1450 or wirelessly connected such as via Bluetooth connectivity. Additional devices such as printers, microphones, speakers, and the like may be connected to the system unit 1410 thereby.

The system unit 1410 may utilize any operating system having a graphical user interface (GUI), such as WINDOWS from Microsoft Corporation of Redmond, Wash., MAC OS from Apple, Inc. of Cupertino, Calif., various versions of UNIX with the X-Windows windowing system, and so forth. The system unit 1410 executes one or more computer programs, with the results thereof being displayed on the display device 1420. Generally, the operating system and the computer programs are tangibly embodied in a computer-readable medium, e.g., the hard drive 1414. Both the operating system and the computer programs may be loaded from the aforementioned data storage devices into the RAM 1412 for execution by the CPU 1411. The computer programs may comprise instructions, which, when read and executed by the CPU 1411, cause the same to perform or execute the steps or features of the various embodiments set forth in the present disclosure.

For example, a program that is installed in the computer 1400 can cause the computer 1400 to function as an apparatus such as the apparatus 200 of FIG. 2. Such a program may act on the CPU 1411 to cause the computer 1400 to function as some or all of the sections, components, elements, databases, engines, interfaces, etc. of the apparatus 200 of FIG. 2 (e.g., the candidate chemical identifier 230, the chemical evaluator 250, etc.). A program that is installed in the computer 1400 can also cause the computer 1400 to perform an operational flow such as those illustrated in FIGS. 6-13. Such a program may act on the CPU 1411 to cause the computer 1400 to perform some or all of the steps of FIG. 7 (e.g., identify candidate chemical(s) S730, determine chemical according to chemical decision mode S740, etc.).

The above-mentioned program may be provided to the hard drive 1414 by or otherwise reside on an external storage medium such as a DVD-ROM, optical recording media such as a Blu-ray Disk or a CD, magneto-optic recording medium such as an MO, a tape medium, a semiconductor memory such as an IC card, a mechanically encoded medium such as a punch card, etc. Additionally, program storage media can include a hard disk or RAM in a server system connected to a communication network such as a dedicated network or the Internet, such that the program may be provided to the computer 1400 via the network. Program storage media may, in some embodiments, be non-transitory, thus excluding transitory signals per se, such as radio waves or other electromagnetic waves.

Instructions stored on a program storage medium may include, in addition to code executable by a processor, state information for execution by programmable circuitry such as a field-programmable gate arrays (FPGA) or programmable logic array (PLA).

Although certain features of the present disclosure are described in relation to a computer 1400 with input and output capabilities including a keyboard 1430 and mouse 1440, specifics thereof are presented by way of example only and not of limitation. Any alternative graphical user interfaces such as touch interfaces and pen/digitizer interfaces may be substituted. The analogs of those features will be readily appreciated, along with suitable modifications to accommodate these alternative interfaces while still achieving the same functionalities.

Along these lines, the foregoing computer 1400 represents only one exemplary apparatus of many otherwise suitable for implementing aspects of the present disclosure, and only the most basic of the components thereof have been described. It is to be understood that the computer 1400 may include additional components not described herein, and may have different configurations and architectures. Any such alternative is deemed to be within the scope of the present disclosure.

The above description is given by way of example, and not limitation. Given the above disclosure, one skilled in the art could devise variations that are within the scope and spirit of the innovations disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A method for identification of chemicals in a sample, the method comprising:
    receiving surface acoustic wave frequency response data generated by a surface acoustic wave sensor of a gas chromatography/surface acoustic wave system, the surface acoustic wave frequency response data including one or more peaks corresponding respectively to one or more eluted components separated from a sample by a gas chromatograph of the gas chromatography/surface acoustic wave system;
    receiving Raman spectrum data generated by a Raman spectrometer for the one or more eluted components;
    producing a Raman spectrum corresponding to an eluted component of interest from among the one or more eluted components based upon an integration of the Raman spectrum data;
    identifying a set of one or more candidate chemicals for the eluted component of interest based on the corresponding peak of the surface acoustic wave frequency response data; and
    searching a Raman database for a match between the produced Raman spectrum and a chemical in the Raman database from among the set of candidate chemicals for the eluted component of interest.

2. The method of claim 1, further comprising:
    calculating a retention index for the eluted component of interest from the corresponding peak of the surface acoustic wave frequency response data, wherein said identifying the set of one or more candidate chemicals for the eluted component of interest includes searching a retention index database for one or more matches between the calculated retention index and chemicals in the retention index database.

3. The method of claim 1, further comprising:
    estimating a mass of the eluted component of interest based on the corresponding peak of the surface acoustic wave frequency response data.

4. The method of claim 3, wherein said estimating the mass includes comparing the peak corresponding to the eluted component of interest to a calibration curve.

5. The method of claim 1, further comprising:
    identifying the one or more peaks of the surface acoustic wave frequency response data; and
    identifying one or more valleys of the surface acoustic wave frequency response data, wherein said producing is based upon an integration of the Raman spectrum data from a valley immediately preceding the peak corresponding to the eluted component of interest to a valley immediately following the peak corresponding to the eluted component of interest.

6. The method of claim 5, further comprising:
    initiating a partial-overlap decision mode based upon an evaluation of adjacent peaks of the one or more peaks being partially overlapping.

7. The method of claim 6, wherein said initiating the partial-overlap decision mode is further based upon i) an evaluation of the height of a valley between the adjacent peaks exceeding a valley height threshold or ii) an evaluation of the adjacent peaks being closer together than a peak distance threshold.

8. The method of claim 6, further comprising:
    producing a front Raman spectrum of the first of the adjacent peaks based upon an integration of the Raman spectrum data from a valley immediately preceding a first of the adjacent peaks to a point prior to a valley between the adjacent peaks;
    producing a distorted Raman spectrum of the second of the adjacent peaks based upon an integration of the Raman spectrum data from the valley between the adjacent peaks to a valley immediately following a second of the adjacent peaks;
    subtracting the produced front Raman spectrum from the distorted Raman spectrum of the second of the adjacent peaks, thereby producing a corrected Raman spectrum of the second of the adjacent peaks;
    identifying a set of one or more candidate chemicals for the eluted component corresponding to the first of the adjacent peaks based on the first of the adjacent peaks;
    identifying a set of one or more candidate chemicals for the eluted component corresponding to the second of the adjacent peaks based on the second of the adjacent peaks;
    searching the Raman database for a match between the produced front Raman spectrum and a chemical in the Raman database from among the set of candidate chemicals for the eluted component corresponding to the first of the adjacent peaks; and
    searching the Raman database for a match between the corrected Raman spectrum of the second of the adjacent peaks and a chemical in the Raman database from among the set of candidate chemicals for the eluted component corresponding to the second of the adjacent peaks.

9. The method of claim 6, further comprising:
    producing a distorted Raman spectrum of the first of the adjacent peaks based upon an integration of the Raman spectrum data from a valley immediately preceding a first of the adjacent peaks to a valley between the adjacent peaks;
    producing a tail Raman spectrum of the second of the adjacent peaks based upon an integration of the Raman spectrum data from a point after the valley between the adjacent peaks to a valley immediately following a second of the adjacent peaks;
    subtracting the produced tail Raman spectrum from the distorted Raman spectrum of the first of the adjacent peaks, thereby producing a corrected Raman spectrum of the first of the adjacent peaks;
    identifying a set of one or more candidate chemicals for the eluted component corresponding to the first of the adjacent peaks based on the first of the adjacent peaks;

identifying a set of one or more candidate chemicals for the eluted component corresponding to the second of the adjacent peaks based on the second of the adjacent peaks;

searching the Raman database for a match between the corrected Raman spectrum of the first of the adjacent peaks and a chemical in the Raman database from among the set of candidate chemicals for the eluted component corresponding to the first of the adjacent peaks; and searching the Raman database for a match between the produced tail Raman spectrum and a chemical in the Raman database from among the set of candidate chemicals for the eluted component corresponding to the second of the adjacent peaks.

10. The method of claim 6, further comprising:

producing a front Raman spectrum of the first of the adjacent peaks based upon an integration of the Raman spectrum data from a valley immediately preceding a first of the adjacent peaks to a point prior to a valley between the adjacent peaks;

producing a tail Raman spectrum of the second of the adjacent peaks based upon an integration of the Raman spectrum data from a point after the valley between the adjacent peaks to a valley immediately following a second of the adjacent peaks;

identifying a set of one or more candidate chemicals for the eluted component corresponding to the first of the adjacent peaks based on the first of the adjacent peaks;

identifying a set of one or more candidate chemicals for the eluted component corresponding to the second of the adjacent peaks based on the second of the adjacent peaks;

searching the Raman database for a match between the produced front Raman spectrum and a chemical in the Raman database from among the set of candidate chemicals for the eluted component corresponding to the first of the adjacent peaks; and searching the Raman database for a match between the produced tail Raman spectrum and a chemical in the Raman database from among the set of candidate chemicals for the eluted component corresponding to the second of the adjacent peaks.

11. The method of claim 5, further comprising:

initiating a non-overlap decision mode based upon an evaluation of the peak corresponding to the eluted component of interest being a combination of two or more fully overlapped peaks.

12. The method of claim 11, wherein said initiating the non-overlap decision mode is further based upon an evaluation of a match to the peak corresponding to the eluted component of interest not being found by said searching.

13. The method of claim 11, further comprising:

searching the Raman database for known Raman spectra of the one or more candidate chemicals for the eluted component of interest; and decomposing the produced Raman spectrum into a combination of the known Raman spectra.

14. The method of claim 13, wherein said decomposing includes subtracting one or more of the known Raman spectra from the produced Raman spectrum and validating that the resulting Raman spectrum is one of the known Raman spectra.

15. The method of claim 1, further comprising:

separating out the one or more eluted components from the sample with the gas chromatograph;

generating the surface acoustic wave frequency response data with the surface acoustic wave sensor; and generating the Raman spectrum data with the Raman spectrometer.

16. The method of claim 15, further comprising aligning the Raman spectrometer with a condensation spot on the surface acoustic wave sensor where the one or more eluted components accumulate after being separated from the sample by the gas chromatograph, wherein said generating the Raman spectrum data includes collecting Raman scattered light from one or more eluted components accumulated at the condensation spot.

17. The method of claim 16, further comprising:

adjusting a temperature of the surface acoustic wave sensor with a thermoelectric cooler based upon a result of an evaluation, with respect to the peak corresponding to the eluted component of interest, of whether a match is found by said searching.

18. A system for identification of chemicals in a sample, the system comprising:

a gas chromatograph;

a surface acoustic wave sensor coupled with the gas chromatograph to define a gas chromatography/surface acoustic wave system in which one or more eluted components separated from a sample by the gas chromatograph accumulate at a condensation spot on the surface acoustic wave sensor; and a Raman spectrometer aligned with the condensation spot, Raman scattered light from one or more eluted components accumulated at the condensation spot being collectable by the Raman spectrometer.

19. The system of claim 18, further comprising:

an input interface communicatively coupled to the surface acoustic wave sensor and the Raman spectrometer, the input interface being receptive to surface acoustic wave frequency response data generated by the surface acoustic wave sensor and including one or more peaks corresponding respectively to the one or more eluted components separated from the sample by the gas chromatograph, the input interface further being receptive to Raman spectrum data generated by the Raman spectrometer for the one or more eluted components;

a spectrum producer communicatively coupled to the input interface, a Raman spectrum corresponding to an eluted component of interest from among the one or more eluted components being produced by the spectrum producer based upon an integration of the Raman spectrum data;

a candidate chemical identifier communicatively coupled to the input interface, a set of one or more candidate chemicals for the eluted component of interest being identified by the candidate chemical identifier based on the corresponding peak of the surface acoustic wave frequency response data; and a Raman search engine communicatively coupled to the candidate chemical identifier and the spectrum producer, a Raman database being searched by the Raman search engine for a match between the produced Raman spectrum and a chemical in the Raman database from among the set of candidate chemicals for the eluted component of interest.

20. A non-transitory program storage medium on which are stored instructions executable by a processor or programmable circuit to perform operations for identification of chemicals in a sample, the operations comprising:

receiving surface acoustic wave frequency response data generated by a surface acoustic wave sensor of a gas chromatography/surface acoustic wave system, the surface acoustic wave frequency response data including one or more peaks corresponding respectively to one or more eluted components separated from a sample by a gas chromatograph of the gas chromatography/surface acoustic wave system;

receiving Raman spectrum data generated by a Raman spectrometer for the one or more eluted components;

producing a Raman spectrum corresponding to an eluted component of interest from among the one or more eluted components based upon an integration of the Raman spectrum data;

identifying a set of one or more candidate chemicals for the eluted component of interest based on the corresponding peak of the surface acoustic wave frequency response data; and searching a Raman database for a match between the produced Raman spectrum and a chemical in the Raman database from among the set of candidate chemicals for the eluted component of interest.

* * * * *